US011873507B2

(12) United States Patent
Wang et al.

(10) Patent No.: US 11,873,507 B2
(45) Date of Patent: Jan. 16, 2024

(54) COMPOSITIONS AND METHODS FOR EXPRESSION OF IL-12 AND IL-1RA

(71) Applicant: Replicate Bioscience, Inc., San Diego, CA (US)

(72) Inventors: Nathaniel Stephen Wang, San Diego, CA (US); Shigeki Joseph Miyake-Stoner, San Diego, CA (US); Parinaz Aliahmad, San Diego, CA (US)

(73) Assignee: Replicate Bioscience, Inc., San Diego, CA (US)

( * ) Notice: Subject to any disclaimer, the term of this patent is extended or adjusted under 35 U.S.C. 154(b) by 0 days.

(21) Appl. No.: 17/537,211

(22) Filed: Nov. 29, 2021

(65) Prior Publication Data

US 2023/0167459 A1 Jun. 1, 2023

(51) Int. Cl.

| | |
|---|---|
| ***C12N 15/86*** | (2006.01) |
| ***C12N 15/24*** | (2006.01) |
| ***C12N 15/62*** | (2006.01) |
| ***A61K 48/00*** | (2006.01) |
| ***A61K 9/51*** | (2006.01) |
| ***C07K 14/54*** | (2006.01) |

(52) U.S. Cl.

CPC ............ *C12N 15/86* (2013.01); *A61K 9/5123* (2013.01); *C07K 14/5434* (2013.01); *C12N 2770/36143* (2013.01)

(58) Field of Classification Search

None

See application file for complete search history.

(56) References Cited

U.S. PATENT DOCUMENTS

| | | | | |
|---|---|---|---|---|
| 2006/0073594 | A1 | 4/2006 | Yao et al. | |
| 2008/0241112 | A1* | 10/2008 | Westenfelder | A61P 15/08 424/93.7 |
| 2010/0099672 | A1 | 4/2010 | Karp et al. | |
| 2011/0300205 | A1 | 12/2011 | Geall et al. | |
| 2012/0213813 | A1* | 8/2012 | Smith | A61P 31/10 424/274.1 |
| 2020/0057048 | A1 | 2/2020 | Santamaria | |
| 2020/0140563 | A1* | 5/2020 | Champion | C07K 16/2878 |
| 2022/0040281 | A1* | 2/2022 | Schwendt | A61K 39/015 |
| 2022/0041724 | A1* | 2/2022 | Twitty | C07K 14/522 |

FOREIGN PATENT DOCUMENTS

WO 2020068261 * 4/2020

OTHER PUBLICATIONS

Ren, H. et al. (2003). "Immunogene therapy of recurrent glioblastoma multiforme with a liposomally encapsulated replication-incompetent Semliki forest virus vector carrying the human interleukin-12 gene—a phase I/II clinical protocol," *Journal of Neuro-Oncology* 64(1-2):147-154.

Chikkanna-Gowda, C.P. et al. (Aug. 2005). "Regression of mouse tumours and inhibition of metastases following administration of a Semliki Forest virus vector with enhanced expression of IL-12," *Gene Therapy* 12(16):1253-1263.

Zhang, J. et al. (Apr. 1997). "Cloning of human IL-12 p40 and p35 DNA into the Semliki Forest virus vector: expression of IL-12 in human tumor cells," *Gene Therapy* 4(4):367-374.

GenBank Accession No. EF151502.1 (Dec. 23, 2006). "Eastern equine encephalitis virus strain FL93-939, complete genome," located at <https://www.ncbi.nlm.nih.gov/nuccore/EF151502> 5 pages.

* cited by examiner

*Primary Examiner* — Maria Marvich

(74) *Attorney, Agent, or Firm* — Mintz, Levin, Cohn, Ferris, Glovsky and Popeo, P.C.

(57) ABSTRACT

The present disclosure relates to the field of molecular virology, and particularly relates to nucleic acid molecules encoding a modified alphavirus virus viral genome or self-replicating RNA (srRNA) construct, pharmaceutical compositions containing the same, and the use of such nucleic acid molecules and compositions for production of desired products in cell cultures or in a living body. Also provided are methods for eliciting a pharmacodynamics effect in a subject.

19 Claims, 14 Drawing Sheets

Specification includes a Sequence Listing.

```
SEQUENCE LISTING


<160> NUMBER OF SEQ ID NOS: 14

<210> SEQ ID NO 1
<211> LENGTH: 197
<212> TYPE: PRT
<213> ORGANISM: Homo sapiens
<220> FEATURE:
<221> NAME/KEY: misc_feature
<223> OTHER INFORMATION: human IL-12 p35 subunit

<400> SEQUENCE: 1

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
```

```
            180                 185                 190

Tyr Leu Asn Ala Ser
        195


<210> SEQ ID NO 2
<211> LENGTH: 219
<212> TYPE: PRT
<213> ORGANISM: Homo sapiens
<220> FEATURE:
<221> NAME/KEY: misc_feature
<223> OTHER INFORMATION: human IL-12 p35 subunit along with its signal
      sequence

<400> SEQUENCE: 2

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215


<210> SEQ ID NO 3
<211> LENGTH: 222
<212> TYPE: PRT
<213> ORGANISM: Homo sapiens
<220> FEATURE:
<221> NAME/KEY: misc_feature
<223> OTHER INFORMATION: human IL-12 p40 subunit

<400> SEQUENCE: 3

Ile Trp Glu Leu Lys Lys Asp Val Tyr Trp Glu Leu Asp Trp Tyr Pro
1               5                   10                  15

Asp Ala Pro Gly Glu Met Trp Leu Thr Cys Asp Thr Pro Glu Glu Asp
            20                  25                  30

Gly Ile Thr Trp Thr Leu Asp Gln Ser Ser Glu Val Leu Gly Ser Gly
        35                  40                  45
```

```
Lys Thr Leu Thr Ile Gln Val Lys Glu Phe Gly Asp Ala Gly Gln Tyr
    50                  55                  60

Thr Cys His Lys Gly Gly Glu Val Leu Ser His Ser Leu Leu Leu Leu
65                  70                  75                  80

His Lys Lys Glu Asp Gly Ile Trp Ser Thr Asp Ile Leu Lys Asp Gln
                85                  90                  95

Lys Glu Pro Asn Lys Thr Phe Leu Arg Cys Glu Ala Lys Asn Tyr Ser
            100                 105                 110

Gly Arg Phe Thr Cys Trp Leu Thr Thr Ile Ser Thr Asp Leu Thr Phe
        115                 120                 125

Ser Val Lys Ser Ser Arg Gly Ser Ser Asp Pro Gln Gly Val Thr Cys
    130                 135                 140

Gly Ala Ala Thr Leu Ser Ala Glu Arg Val Arg Gly Asp Asn Lys Glu
145                 150                 155                 160

Tyr Glu Tyr Ser Val Glu Cys Gln Glu Asp Ser Ala Cys Pro Ala Ala
                165                 170                 175

Glu Glu Ser Leu Pro Ile Glu Val Met Val Asp Ala Val His Lys Leu
            180                 185                 190

Lys Tyr Glu Asn Tyr Thr Ser Ser Phe Phe Ile Arg Asp Ile Ile Pro
        195                 200                 205

Asp Pro Pro Lys Asn Leu Asp Leu Phe Pro Leu Ile Trp Ser
    210                 215                 220


<210> SEQ ID NO 4
<211> LENGTH: 328
<212> TYPE: PRT
<213> ORGANISM: Homo sapiens
<220> FEATURE:
<221> NAME/KEY: misc_feature
<223> OTHER INFORMATION: human IL-12 p40 subunit along with its signal
      sequence

<400> SEQUENCE: 4

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
```

-continued

```
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 5
<211> LENGTH: 177
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: human IL-1RA encoded by IL1RN transcript 1

<400> SEQUENCE: 5

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu


<210> SEQ ID NO 6
```

<211> LENGTH: 180
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: human IL-1RA encoded by IL1RN transcript 2

<400> SEQUENCE: 6

```
Met Ala Leu Ala Asp Leu Tyr Glu Glu Gly Gly Gly Gly Gly Gly Glu
1               5                   10                  15

Gly Glu Asp Asn Ala Asp Ser Lys Glu Thr Ile Cys Arg Pro Ser Gly
            20                  25                  30

Arg Lys Ser Ser Lys Met Gln Ala Phe Arg Ile Trp Asp Val Asn Gln
        35                  40                  45

Lys Thr Phe Tyr Leu Arg Asn Asn Gln Leu Val Ala Gly Tyr Leu Gln
    50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
            100                 105                 110

Ile Thr Asp Leu Ser Glu Asn Arg Lys Gln Asp Lys Arg Phe Ala Phe
        115                 120                 125

Ile Arg Ser Asp Ser Gly Pro Thr Thr Ser Phe Glu Ser Ala Ala Cys
    130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

<210> SEQ ID NO 7
<211> LENGTH: 159
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: human IL-1RA encoded by IL1RN transcript 3

<400> SEQUENCE: 7

```
Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
```

-continued

```
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155


<210> SEQ ID NO 8
<211> LENGTH: 143
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: human IL-1RA encoded by IL1RN transcript 4

<400> SEQUENCE: 8

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Val Pro Ile Glu Pro His Ala Leu Phe
        35                  40                  45

Leu Gly Ile His Gly Gly Lys Met Cys Leu Ser Cys Val Lys Ser Gly
    50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Phe Gln Glu Asp Glu
    130                 135                 140


<210> SEQ ID NO 9
<211> LENGTH: 159
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: human intracellular IL-1RA, icIL-1Ra

<400> SEQUENCE: 9

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80
```

-continued

```
Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155
```

<210> SEQ ID NO 10
<211> LENGTH: 10907
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: Exemplary construct

<400> SEQUENCE: 10

```
gatagggtac ggtgtagagg caaccaccct atttccacct atccaaaatg gagaaagttc     60

atgttgactt agacgcagac agcccattcg tcaagtcact gcaaagatgc tttccacatt    120

ttgagataga agcaacgcag gtcactgaca atgaccatgc taatgctagg gcgttttcgc    180

acctagctac taagctcatt gagggagaag tggatacaga ccaggtgatc ctggatattg    240

ggagcgcgcc tgtaaggcac acgcattcca aacataagta ccactgcatt tgcccaatga    300

aaagcgcaga agaccctgac agactctacc gctatgcaga caagcttaga aaaagtgatg    360

tcactgacaa atgtattgcc tctaaggccg cggacctgct aacagtaatg tcgacgcctg    420

acactgagac accctcgtta tgcatgcaca ctgactcaac ttgccggtac cacggctccg    480

tggccgtata tcaggatgta tatgcagtgc atgcaccgac ttccatttac taccaggcgc    540

tgaaaggtgt acgaactatc tattggatcg ggtttgatac tacaccgttc atgtacaaga    600

acatggcagg cgcctaccct acatacaaca caaattgggc cgatgaaagt gtgttggaag    660

ccagaaatat agggctgggt agttcagact tgcacgaaaa gagtttcgga aaagtatcca    720

ttatgaggaa gaagaaatta caacccacta ataaagtaat attttctgtg ggtcaacta     780

tttatactga agagagaata ctgttacgca gttggcatct acctaatgtc tttcatctaa    840

aaggtaaaac tagctttaca ggcagatgta acaccatcgt cagctgcgaa ggttacgttg    900

tcaagaagat tacgctcagt cctgggattt acgggaaagt ggataatctt gcttcgacca    960

tgcaccgaga gggattctta agttgcaagg ttacagacac gttaagaggg gagagggtct   1020

ctttccccgt atgtacgtac gtgccagcga cactgtgcga ccagatgacc gggatactgg   1080

cgactgacgt cagtgtcgat gacgcccaga agctgctggt tgggctcaac cagcgaattg   1140

tcgtcaatgg cagaacacaa cgtaacacaa ataccatgca gaattatcta ttaccagtgg   1200

tcgcccaggc gttctcgcgg tgggcgcggg aacaccgcgc agacctggag gacgaaaaag   1260

ggctaggggt acgggaacgt tccctagtca tgggctgctg ctgggctttc aaaactcaca   1320

agatcacatc catttacaag agacctggga ctcaaactat caagaaggtg cccgccgtat   1380

tcaattcctt cgtcatccca caaccaacca gctatgggct tgatatagga ttgcgtcgcc   1440

gaattaagat gctattcgac gcaaagaagg cacccgctcc aattattact gaggccgacg   1500

tcgcacacct taaaggcctg caggatgaag ctgaagccgt ggctgaggct gaagccgtgc   1560
```

-continued

```
gtgcagcact acctccactt ctgccggagg tcgataagga gaccgtagag gccgatatcg   1620
acctgatcat gcaggaggca ggagcaggca gcgtggagac acctagacga cacatcaagg   1680
tcacgacgta tccaggagaa gaaatgatcg gctcgtacgc agtgctctca ccacaagcgg   1740
tccttaacag cgagaagcta gcttgcattc acccgttagc tgagcaagtg ctcgtgatga   1800
ctcacaaagg gcgcgcagga cgatacaagg tagagccata ccacggtaga gttatcgtcc   1860
ctagtggtac agctatacca atccccgatt tccaggctct gagtgaaagt gcaaccatag   1920
tatttaacga acgggagttc gttaaccgtt acttacacca cattgccgtt aacggagggg   1980
cattgaatac agatgaagag tactacaagg ttgtgaaaag cactgagaca gactctgagt   2040
acgtatttga catcgacgca aagaagtgcg tgaagaaagg ggatgccgga ccaatgtgcc   2100
tggtcggcga gttagtagac ccgccattcc acgaatttgc gtacgagagt ttaaaaacac   2160
gtcctgctgc accacacaaa gtgcctacta tcggagtcta tggagtccca ggttccggaa   2220
agtctggtat aatcaaaagc gctgttacca agcgtgatct ggtggtcagt gcaaagaaag   2280
aaaattgcat ggaaatcatt aaagacgtca aacgtatgcg cggcatggac atcgccgccc   2340
gcacagtgga ttcggtgctg ctaaatgggg taaaacactc cgtcgacaca ctgtacatag   2400
acgaggcatt cgcttgccat gcagggaccc tgctagcact tatcgccatc gtcaagccaa   2460
agaaagttgt attgtgtgga gatccgaaac aatgcggctt ctttaacatg atgtgtctaa   2520
aagtacattt taaccacgag atatgcacag aagtgtatca caagagtatt tctcggcgat   2580
gcactaagac agtgacatcc attgtttcta ccctgttcta tgataaacgg atgagaactg   2640
tcaacccatg caatgataag atcataatag ataccaccag tactaccaaa cctttaaagg   2700
atgacataat attaacctgc tttagagggt gggttaagca actgcagatt gactacaaga   2760
accacgagat catgaccgca gcggcctcac aggggcttac tagaaaaggg gtatacgcag   2820
tgcgctacaa ggtcaatgag aacccactat acgcacagac atctgagcat gtgaatgtat   2880
tacttacacg cacagaaaaa cgtatagtat ggaagacttt ggccggtgac ccttggatca   2940
agacgttgac agcatcgtat ccgggtaatt tcaccgccac actggaagaa tggcaagctg   3000
agcatgacgc tatcatggcg aaaatacttg agacaccagc tagcagcgac gttttccaaa   3060
ataaagtgaa catctgctgg gccaaagcgc tagaacctgt gttggccacc gccaatatta   3120
cgctgacccg ctcgcagtgg gagactattc cagcgttcaa ggatgacaaa gcgtattcgc   3180
ctgagatggc cttaaacttt ttctgcacca gattctttgg tgtcgacatc gacagcgggt   3240
tgttctccgc gccaactgtt ccgctgactt acaccaatga acactgggat aatagcccag   3300
gtccaaacat gtatgggttg tgcatgcgca ctgctaaaga acttgcacgt cggtatcctt   3360
gtattctgaa agccgtggat acaggtagag tggctgacgt tcgcacagac actatcaaag   3420
actataaccc gctaataaat gtggtacccc ttaatagaag actcccacac tcgttggttg   3480
tcacacacag atacactggg aacggtgatt actcccagct agtgactaag atgaccggaa   3540
aaaccgtact cgtagtgggt acacctatga acataccagg aaagagagtt gagacattag   3600
gcccaagccc acaatgtaca tataaagcgg aattggacct gggcattcct gccgctttag   3660
gcaaatatga catcatcttt attaacgtga ggactcccta ccgacaccac cactaccaac   3720
agtgcgagga ccatgcgatc caccacagca tgcttaccag aaaagcagtg gaccatttga   3780
acaaaggcgg tacgtgcatc gcattgggct atgggactgc ggacagagcc accgagaaca   3840
ttatctctgc agtcgcccgc tcattcaggt tctcacgtgt gtgccagccg aagtgtgcct   3900
```

-continued

```
gggaaaacac tgaggtcgcg ttcgtgtttt tcggcaagga caacggcaac catctccaag   3960
atcaagatag gctgagtgtt gtgttaaaca acatatacca agggtcaact caacatgaag   4020
ctggcagagc acctgcgtat agagtggtgc gcggcgacat aacaaagagc aatgatgagg   4080
ttattgttaa cgcggcgaac aacaaagggc aacctggtgg cggtgtgtgt ggcgcccttt   4140
acaggaagtg gcctggagct tttgacaagc agccggtagc aactggtaaa gcgcacctcg   4200
tcaagcattc tccgaacgtc atccatgccg ttggccctaa tttttctagg ctatcagaaa   4260
acgaaggaga ccagaaattg tctgaagtgt acatggacat tgccagaatt atcaacaacg   4320
agaggtttac taaagtctcc attccgttgt tatctaccgg catttacgca ggtggtaagg   4380
acagggttat gcaatcgctg aaccatttat tcacagccat ggatactacc gacgcagaca   4440
tcaccattta ctgtctagat aagcaatggg agtcaagaat aaaggaagct atcacccgga   4500
aggaaagtgt tgaagaactt actgaggatg acagaccagt tgacattgaa ctggtacggg   4560
tgcacccgtt gagcagcttg gcaggtagac ctggttattc aaccaccgag ggcaaggtgt   4620
attcgtacct agaggggact aggtttcacc aaactgccaa agacatagct gaaatttacg   4680
ctatgtggcc taacaagcaa gaagcaaacg agcagatttg cttatatgtg ttgggagaga   4740
gtatgaacag catccgctct aagtgtccag ttgaagagtc ggaggcctct tccccccctc   4800
acaccatccc gtgtctgtgc aactatgcaa tgactgcaga gcgagtttac agattacgta   4860
tggcgaagaa tgaacaattc gcagtttgtt cgtcctttca gttaccgaaa tacaggatta   4920
caggggttca gaaaattcaa tgcagtaaac ctgtgatatt ctccggcact gtaccaccgg   4980
ccatacatcc aagaaaattc gcatctgtga cagtggaaga cactccggtg gtccaacctg   5040
aaaggttggt gcctaggcga cctgcaccgc ctgtgcccgt acctgcaaga atccccagcc   5100
ctccatgtac atcgaccaac ggatcgacga ccagtataca atcactgggg gaggatcaaa   5160
gcgcatctgc ttctagcgga gctgaaatct ctgtagacca ggtttcgcta tggagcatac   5220
ccagcgctac tgggttcgat gtgcgtacct cctcatcgtt gagtctagag cagtctacct   5280
ttccgacaat ggttgtcgaa gcagagattc acgccagtca aggatcactg tggagtatac   5340
ccagtatcac cggatctgaa acccgcgttc cgtcacctcc aagtcagggt agcagacatt   5400
ccaccccatc tgtaagtgct tcacacacgt ccgtggactt aatcacgttt gacagcgttg   5460
cagagatttt ggaagatttc agtcgttcgc cgtttcaatt tttgtctgaa atcaaaccta   5520
tccctgcacc tcgtacccga gttaataaca tgagccgcag cgcagacacg atcaaaccaa   5580
ttccaaagcc gcgtaaatgc caggtgaagt acacgcagcc acctggcgtc gccagggcca   5640
tatcggcagc ggaatttgac gagtttgtgc ggaggcactc gaattgacgg tacgaagcgg   5700
gcgcgtacat tttctcatcc gagacaggac aagggcacct gcaacaaaaa tccacgcggc   5760
aatgcaaact ccagtatcca atcctggagc gttccgtcca tgagaaattt tacgccccgc   5820
gcctcgatct cgagcgtgag aagctgttgc agaagaaact acaattgtgt gcttctgaag   5880
gtaatcggag caggtatcag tctcgtaaag tagagaacat gaaggcaatc accgttgagc   5940
gtctactgca ggggataggc tcatatctct ctgcagaacc gcaaccagtt gaatgctaca   6000
aagtcaccta tcctgctccc atgtattcaa gtactgcaag caacagcttt tcatcagcag   6060
aagtggccgt caaagtctgc aacctagtac tgcaagagaa ttttcccacc gtagccagct   6120
ataacataac ggatgagtat gatgcctatc ttgacatggt ggacggagca tcctgctgtt   6180
tagatactgc cactttttgc ccagctaaat tgaggagctt tccaaagaag cacagttatt   6240
tgcggcctga gatacgatca gcagtgccat caccgattca aaacacgctc cagaatgtac   6300
```

-continued tagcagcagc cacgaaacgg aattgcaatg tcactcaaat gagggaactt ccagtgttgg 6360
attcagctgc cttcaacgtg gagtgtttca aaaagtacgc ctgtaacgat gagtactggg 6420
acttctacaa gacaaacccg ataagactca ccgcagaaaa tgttactcag tatgttacta 6480
agttaaaggg acccaaagca gctgcccttt ttgcgaaaac gcataactta cagccattgc 6540
atgagatacc aatggataga ttcgtgatgg accttaaacg ggatgtcaag gtcacacccg 6600
ggacaaaaca tactgaagaa agaccaaaag ttcaggtgat acaggcagct gatccacttg 6660
caaccgccta cctatgtggt atacatcgag agcttgtgcg caggttgaac gcagtgctgc 6720
taccgaatat ccacactttg tttgacatgt ctgcagaaga ttttgatgct atcattgccg 6780
aacactttca attcggcgac gcggtgttag agacagacat agcttctttt gataaaagcg 6840
aggacgatgc tatcgccatg tccgctctaa tgattcttga agacctagga gttgatcagg 6900
cactgttaaa cctaattgag gcagcctttg ggaacataac atctgtgcac ttaccaacag 6960
gcacccgatt taagttcggg gcaatgatga aatctgggat gtttttgaca ctctttatca 7020
ataccgttgt caatatcatg atcgctagcc gcgtgctccg cgagcggctg accacttccc 7080
cctgcgcagc atttatcggc gacgacaaca tcgtgaaagg ggttacatct gacgcgctga 7140
tggcagagcg gtgcgccacg tggttgaaca tggaagtgaa gatcatcgat gcagtagtcg 7200
gagtaaaggc accgtacttt tgcggagggt tcatcgtagt cgatcagatt acaggaactg 7260
cgtgcagagt cgccgacccc ctgaagagac tgtttaagct aggtaagccg cttccactgg 7320
acgatgacca agacgtcgac aggcgcagag ctctgcatga tgaagcggca cgttggaaca 7380
gaattggcat caccgaagaa ctggtgaaag cagttgaatc acgctacgag gtgaactacg 7440
tgtcactaat catcacagcg ttgaccacat tagcatcttc agttagcaac tttaaacaca 7500
taagaggtca ccccataacc ctctacggct gacctaaata ggttgtgcat tagtacctaa 7560
cctatttata ttatattgct atctaaatat cagagctgga gacgtggagg agaaccctgg 7620
acctatggaa atctgccggg gacttcgaag ccacctcatc acgttgcttt tgtttctgtt 7680
tcattcagag acgatatgta ggccttcagg tagaaagtct agtaagatgc aggctttccg 7740
gatatgggac gtcaatcaga agacatttta tctcaggaat aatcaacttg ttgccggata 7800
cctgcaaggc ccgaatgtaa atctcgaaga aaaaatcgac gtagtaccga ttgaacctca 7860
tgcactgttt ctgggaatac acgggggaaa gatgtgcctg agttgcgtaa aatccggaga 7920
tgagactcgg ctgcaactcg aagccgtaaa tattacggat ctcagtgaga acagaaagca 7980
ggacaagaga ttcgctttca tacggtctga tagtggcccc actactagtt ttgaaagcgc 8040
cgcgtgccca gggtggttct tgtgtaccgc tatggaagcg gaccagccgg ttagcttgac 8100
taatatgcct gacgaaggag ttatggtaac gaagttctat ttccaggagg atgagtagcc 8160
cctctccctc ccccccccct aacgttactg gccgaagccg cttggaataa ggccggtgtg 8220
cgtttgtcta tatgttattt tccaccatat tgccgtcttt tggcaatgtg agggcccgga 8280
aacctggccc tgtcttcttg acgagcattc ctaggggtct ttcccctctc gccaaaggaa 8340
tgcaaggtct gttgaatgtc gtgaaggaag cagttcctct ggaagcttct tgaagacaaa 8400
caacgtctgt agcgaccctt tgcaggcagc ggaacccccc acctggcgac aggtgcctct 8460
gcggccaaaa gccacgtgta taagatacac ctgcaaaggc ggcacaaccc cagtgccacg 8520
ttgtgagttg gatagttgtg gaaagagtca aatggctctc ctcaagcgta ttcaacaagg 8580
ggctgaagga tgcccagaag gtaccccatt gtatgggatc tgatctgggg cctcggtgca 8640

-continued

```
catgctttac atgtgtttag tcgaggttaa aaaacgtcta ggccccccga accacgggga   8700
cgtggttttc ctttgaaaaa cacgatgata atattgccac aaccatgtgt catcaacagt   8760
tggtgatctc ctggtttagc ttggtgttcc tcgcctcacc cctggttgcc atatgggagc   8820
ttaaaaagga cgtgtatgtc gttgagttgg actggtatcc tgacgcgcct ggcgagatgg   8880
tagttcttac gtgtgataca cccgaagaag acggtataac gtggaccctt gatcagtcat   8940
ctgaagtcct cgggagtgga aagacgctca caatccaggt caaggagttt ggagacgccg   9000
ggcagtacac atgccataaa ggtggtgagg tactctcaca tagcctgctg ctcctccaca   9060
aaaaggagga cgggatctgg tctactgaca tcttgaaaga ccagaaggag cccaagaaca   9120
agacattcct tcgctgcgag gcgaagaact actctggcag gttcacatgc tggtggctca   9180
ccaccatctc aacggacttg actttcagtg ttaagtcctc ccgaggaagt tccgaccctc   9240
aaggggtcac ttgcggtgct gctacgcttt ccgctgagcg cgtgaggggc gacaacaagg   9300
aatatgaata ctccgtagag tgtcaggagg acagtgcatg cccagctgca gaagaaagtc   9360
ttcccattga ggttatggta gatgccgttc acaagctgaa atatgagaac tacacaagct   9420
ctttctttat acgggacata ataaagccag atccaccgaa gaatctccag ctgaaacccc   9480
ttaaaaatag tcgacaagtt gaagtttctt gggaataccc agacacatgg tcaacgcccc   9540
acagctattt tagtctcact ttctgcgtcc aagtacaggg aaagagcaaa agagaaaaaa   9600
aagacagagt cttcaccgat aagactagcg ccacagtgat ttgtcgcaaa aacgcctcta   9660
tctctgtgcg ggcacaggac cgctactact ctagcagttg gtctgagtgg gcctctgtac   9720
cgtgctctgg gtcaggcgct acgaactttt cacttctcaa gcaggcggga gatgtcgagg   9780
aaaatcctgg acccatgtgc cccgcaaggt cattgctcct cgttgcaacc ttggtcctcc   9840
tggatcattt gtcccttgcc cggaacctcc ctgtagcaac gcccgacccc gggatgttcc   9900
cttgcctgca tcacagtcaa aacttgctta gggcggtgtc taacatgttg cagaaagctc   9960
gacaaaccct ggagttttac ccatgcacct ctgaagaaat cgaccatgaa gacatcacca  10020
aggataaaac cagcacagta gaggcatgtc ttccgctgga actgactaag aatgaatctt  10080
gtctgaactc cagggaaaca tcattcatca caaacggttc ctgcctcgca agtcgaaaaa  10140
cgagttttat gatggcattg tgcctgtcct caatatatga agacctgaag atgtatcagg  10200
tagagtttaa gactatgaat gcaaaacttc tgatggatcc gaaacgacag atctttttgg  10260
accagaatat gttggctgta atcgatgaac ttatgcaagc attgaatttc aattctgaga  10320
ctgtacctca gaagtctagt cttgaagaac ccgactttta caaaactaag ataaaactct  10380
gcatattgct tcatgcgttc aggatcagag cagtcactat agaccgggta atgtcatacc  10440
tcaacgcctc ttgaccgcta cgccccaatg acccgaccag ctaacatctt gtcaaccaca  10500
taacactaca ggcagtgtat aaggctgtct tactaaacac taaattcacc ctagttcgat  10560
gtacttccga gctatggtga cggtggtgca taatgccgcc gatgcagtgc ataaggctgc  10620
tatattacca aattataaca ctaagggcag tgcataatgc tgctcctaag taattttata  10680
cacactttat aatcaggcat aattgccgta tatacaatta cactacaggt aatataccgc  10740
ctcttataaa cactacaggc agcgcataat gctgtctttt atatcaattt acaaaatcat  10800
attaattttt tcttttatgt ttttattttg tttttaatat ttcaaaaaaa aaaaaaaaaa  10860
aaaaaaaaaa aaaaaaaaaa aaaaaaaaaa aaaaaaaaaa aaaaaaa                 10907
```

<210> SEQ ID NO 11
<211> LENGTH: 29

-continued

```
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: 5' adaptor sequence

<400> SEQUENCE: 11

ctggagacgt ggaggagaac cctggacct                                29


<210> SEQ ID NO 12
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: 3' adaptor sequence

<400> SEQUENCE: 12

gaccgctacg ccccaatgac ccgaccagc                                29


<210> SEQ ID NO 13
<211> LENGTH: 18
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: bacteriophage T7 RNA polymerase promoter

<400> SEQUENCE: 13

taatacgact cactatag                                            18


<210> SEQ ID NO 14
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<223> OTHER INFORMATION: T7 terminator sequence

<400> SEQUENCE: 14

aacccctctc taaacggagg ggttttttt                                29
```

COMPOSITIONS AND METHODS FOR EXPRESSION OF IL-12 AND IL-1RA

INCORPORATION BY REFERENCE OF SEQUENCE LISTING

The instant application contains a Sequence Listing which has been submitted electronically in ASCII format and is hereby incorporated by reference in its entirety. Said ASCII copy, created on Nov. 29, 2021, is named 058462-508F01US_SL.txt and is 32400 bytes in size.

FIELD

The present disclosure relates to the field of molecular virology and immunology, and particularly relates to the use of nucleic acid molecules encoding modified alphavirus viral genomes and self-replicating RNA (srRNA), pharmaceutical compositions containing the same, and the use of such nucleic acid molecules and compositions for production of desired products in cell cultures or in a living body. Also provided are methods for inducing at least one pharmacodynamic effect in a subject.

BACKGROUND

Interleukin-12 (IL-12) is a pleiotropic proinflammatory cytokine that is produced in response to infection by a variety of cells of the immune system, including phagocytic cells, B cells and activated dendritic cells (Colombo and Trinchieri (2002), Cytokine & Growth Factor Reviews, 13: 155-168). IL-12 plays an essential role in mediating the interaction of the innate and adaptive arms of the immune system, acting on T-cells and natural killer (NK) cells, enhancing the proliferation and activity of cytotoxic lymphocytes and the production of other inflammatory cytokines, especially interferon-γ. IL-12 is a heterodimeric molecule composed of an α-chain (the p35 subunit, IL-12A) and a β-chain (the p40 subunit, IL-12B) covalently linked by a disulfide bridge to form the biologically active 74 kDa heterodimer.

The presence of endogenous IL-12 has been shown to be necessary for immunological resistance to a broad array of pathogens, as well as to transplanted and chemically induced tumors (Gateley et al. (1998), Annu. Rev. Immunol., 16: 495-521). IL-12 has been demonstrated to have a potent anti-tumor activity based upon the induction of IFN-γ and the activation of effector cells such as CD8+ T-cells and NK cells (Brunda of al. (1993), J. Exp. Med., 178: 1223-30). High levels of IFN-gamma are produced by T cells and NK cells in response to IL-12 (Kobayashi et al., 1989, J Exp Med; 170: 827-45), leading to enhanced antigen-presentation through paracrine upregulation of MHC class I and class II expression (Wallach et al., 1982 Nature 1982; 299:833-69). As a result of its demonstrated anti-tumor activity, IL-12 has been tested in human clinical trials as an immunotherapeutic agent for the treatment of a wide variety of cancers (Atkins et al. (1997), Clin. Cancer Res., 3: 409-17; Gollob et al. (2000), Clin. Cancer Res., 6: 1678-92; and Hurteau et al. (2001), Gynecol. Oncol., 82: 7-10), including renal cancer, colon cancer, ovarian cancer, melanoma and T-cell lymphoma, and as an adjuvant for cancer vaccines (Lee et al. (2001), J. Clin. Oncol. 19: 3836-47).

Systemic administration of IL-12 has principally shown efficacy against some solid tumors but its use in therapy is limited because of its dose-limiting toxicity (Gollob et al., 2000, Clin. Cancer Res. 6:1678-1692). After over a decade in early clinical development, documented cases of severe toxicity and generally low response rates to recombinant IL-12 have prevented its clinical development so far.

Interleukin-1 is also important in immune responses, however, it is the inhibition of this cytokine that has shown much interest. The mode of action of IL-1 can be mediated by interleukin-1 receptor antagonist protein (IL-1ra; also known as "IRAP"). IL-1ra binds to the same receptor on the cell surf ace as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu Rev. Immunol. 16:27-55. Production of IL-1ra is stimulated by several substances including adherent immunoglobulin G (IgG), other cytokines, and bacterial or viral components. IL-1ra is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Patent Application Publication No. 2005/0197293, Mellis et al., published Sep. 8, 2005 In addition, methods for producing IL-1ra from body fluids, including the use of autologous fluids, are described in U.S. Pat. No. 6,623,472, Reineke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

IL-1ra has been delivered as part of a composition with hyaluronic acid, as described in U.S. Pat. No. 6,096,728, Collins et al., issued Aug. 1, 2000. However, many such methods and compositions are associated with issues regarding stability and half-life of IL-1ra as well as the amount and rate of IL-1ra provided. Accordingly, improved compositions and methods of delivering IL-1ra are desirable.

The disclosure provided here provides solutions to the problems existing with previous attempts to deliver IL-12 and IL-1RA and potentially offers improved methods for treatment of conditions including cancer and infection.

SUMMARY

The present disclosure relates generally to the development of immuno-therapeutics, such as recombinant nucleic acid constructs and pharmaceutical compositions including the same for use in the prevention and management of various health conditions. In particular, as described in greater detail below, some embodiments of the disclosure provide nucleic acid constructs containing sequences that encode a modified alphavirus genome or self-replicating RNA (srRNA) where at least a portion of the nucleic acid sequence encoding the viral structural proteins of the modified alphavirus genome or srRNA has been replaced by a coding sequence for a polypeptide construct comprising a) a coding sequence for a p35 subunit of interleukin 12 (p35 or IL-12A) or a functional variant thereof; b) a coding sequence for a subunit 40 of interleukin 12 (p40 or IL-12B)

or functional variant thereof; and c) a coding sequence for an interleukin-1 receptor antagonist (IL-1RA) or a functional variant thereof. Also disclosed are recombinant cells that have been engineered to include one or more of the nucleic acid constructs disclosed herein, methods for producing a molecule of interest, and pharmaceutical compositions including one or more of the following: (a) a nucleic acid construct of the disclosure, (b) a recombinant cell of the disclosure, or (c) a pharmaceutical composition of the disclosure. Further provided in particular aspects of the disclosure are compositions and methods for inducing at least one pharmacodynamic effect in a subject. The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

In one aspect of the disclosure, provided herein are nucleic acid constructs including a nucleic acid sequence encoding a modified alphavirus genome or srRNA, wherein at least a portion of the nucleic acid sequence encoding the viral structural proteins of the modified alphavirus genome or srRNA has been replaced by a coding sequence for a polypeptide construct comprising a) a coding sequence for a p35 subunit of interleukin 12 (p35 or IL-12A) or a functional variant thereof; b) a coding sequence for a p40 subunit of interleukin 12 (p40 or IL-12B) or functional variant thereof; c) a coding sequence for an interleukin-1 receptor antagonist (IL-1RA) or a functional variant thereof, wherein the coding sequences for IL-12A, IL-12B, and IL-1RA are operably linked to one another.

In some embodiments, the modified alphavirus genome or srRNA comprises no nucleic acid sequence encoding viral structural proteins.

In some embodiments, the nucleic acid sequence encoding the modified alphavirus or srRNA is operably linked to a promoter sequence. In some embodiments, the promoter sequence is a 26S subgenomic (sg) promoter.

In some embodiments, the coding sequences of (a) through (c) are operably linked to one another within a single open reading frame (i.e., in a polycistronic ORF).

In some embodiments, the coding sequences of (a) through (c) are operably linked to one another by one or more connector sequences encoding for an autoproteolytic peptide or an internal ribosomal entry site (IRES). In some embodiments, the autoproteolytic peptide comprises one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof. In some embodiments, the IRES is from a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, and a c-myc IRES.

In some embodiments, the modified alphavirus genome or srRNA is of an alphavirus belonging to the VEEV/EEEV group, or the SFV group, or the SINV group.

In some embodiments, the polypeptide construct comprises, in N-terminus to C-terminus direction: a) an IL-12A polypeptide, an IL-12B polypeptide, and an IL-1RA polypeptide; or b) an IL-1RA polypeptide, an IL-12B polypeptide, and an IL-12A polypeptide; wherein the IL-12A, IL-12B, and IL-1RA polypeptides are operably linked to one another by one or more autoproteolytic cleavage sequences or internal ribosomal entry sites.

In some embodiments, the nucleic acid sequence has at least 80%, at least 85%, at least 90%, at least 95%, at least 96%, at least 97%, at least 98%, at least 99%, or 100% sequence identity to SEQ ID NO: 10.

In one aspect, provided herein are recombinant cells including a nucleic acid construct as disclosed herein. In some embodiments, the recombinant cell is a mammalian cell or an insect cell.

In yet another aspect, provided herein are pharmaceutical compositions including a pharmaceutically acceptable excipient and a nucleic acid construct of the disclosure.

In some embodiments, the composition is formulated is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof. In some embodiments, the LNP delivery system comprises a cationic lipid, an ionizable cationic lipid, an anionic lipid, or a neutral lipid. In some embodiments, the lipid is present in mass ratio of lipid to RNA from about 100:1 to about 4:1. In some embodiments, the lipid-based nanoparticles have an average diameter of about 25 nm to about 1000 nm. In some embodiments, the composition is formulated as a biotherapeutic.

In another aspect, provided herein is a method for inducing at least one pharmacodynamic effect in a subject. The method includes administering to the subject a composition comprising a nucleic acid construct of the disclosure. In some embodiments, the administered composition results in induced production of one or more of the following: immune responses and mediators such as interferon gamma (IFNγ). In some embodiments, the at least one pharmacodynamic effect comprises one or more of the following: immunogenicity effect, a biomarker response, a therapeutic effect, a prophylactic effect, a desired effect, an undesired effect, an adverse effect, and effect in a disease model. In some embodiments, the administered composition enhances anti-tumor immunity in a tumor microenvironment. In some embodiments, the subject has a cancer, an immune disease, or a chronic infection. In some embodiments, the composition is administered to the subject individually as a single therapy (monotherapy) or as a first therapy in combination with at least one additional therapies.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows the results from an IL-12 ELISA. The x-axis shows different constructs tested. FIG. 1B shows the results from an IL-RA ELISA. The x-axis shows different constructs tested.

FIG. 2A shows results from an IL-12 bioassay. The x-axis shows different constructs tested. FIG. 2B shows results from an IL-1RA bioactivity assay. The x-axis shows different constructs tested.

FIG. 4A shows the results from an IL-12 ELISA. The x-axis shows different constructs tested. FIG. 4B shows the results from an IL-RA ELISA. The x-axis shows different constructs tested.

FIG. 5A shows the results from an IL-12 bioassay. The x-axis shows different constructs tested. FIG. 5B shows the results from an IL-RA bioassay. The x-axis shows different constructs tested.

FIG. 7A shows the results from an IL-12 ELISA. The x-axis shows different constructs tested. FIG. 7B shows the results from an IL-1RA ELISA. The x-axis shows different constructs tested.

FIG. 8A shows the results from an IL-12 ELISA. The x-axis shows different constructs and formulations tested. FIG. 8B shows the results from an IL-1RA ELISA. The x-axis shows different constructs and formulations tested.

DETAILED DESCRIPTION OF THE DISCLOSURE

Figure 1A:
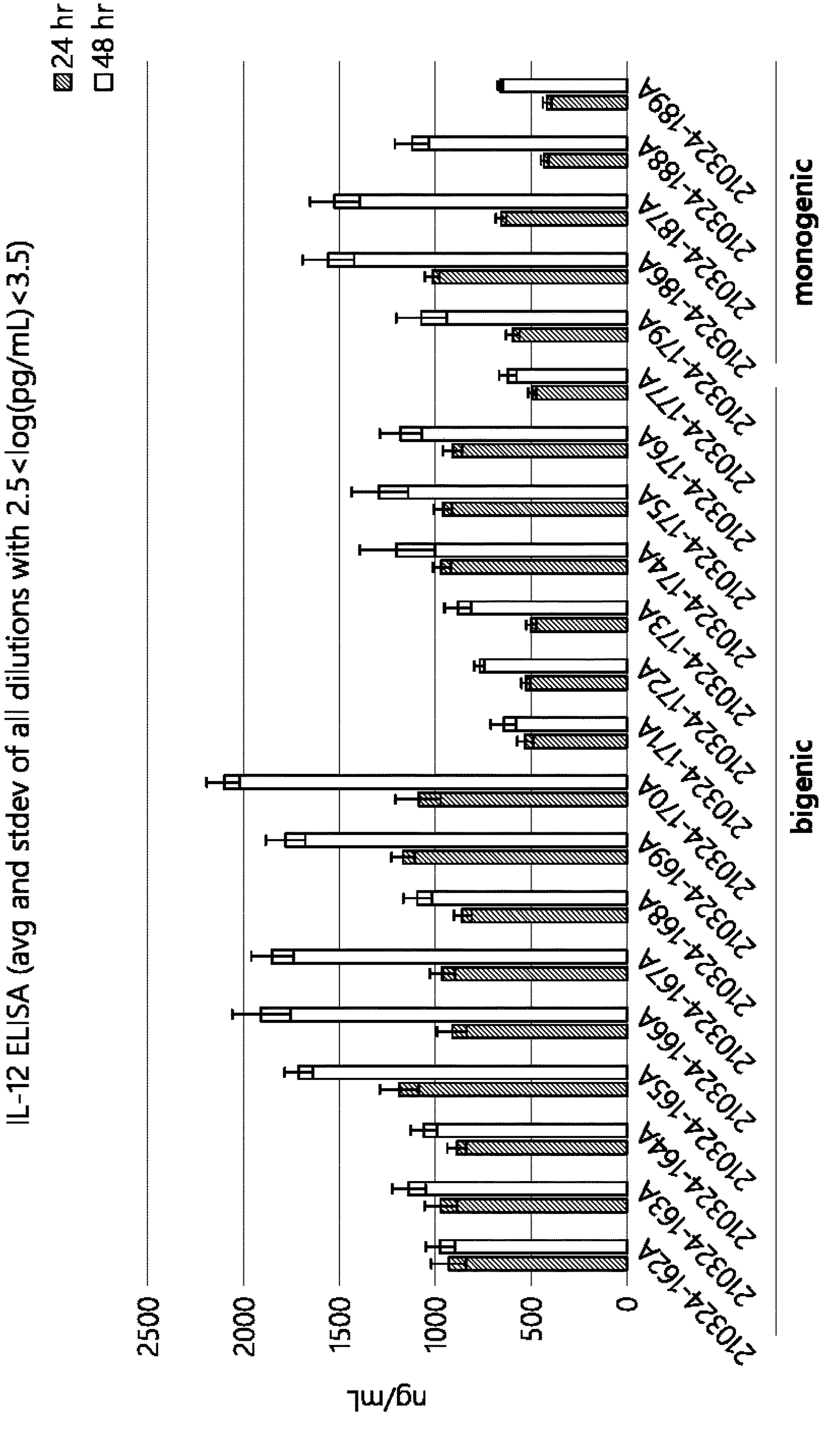
FIGS. 1A-1B are graphical representations of in vitro protein expression from monogenic and multigenic VEE srRNA constructs. Supernatants of transfected BHK-21 cells with each srRNA construct were used to measure protein expression determined by ELISA.
Figure 1B:
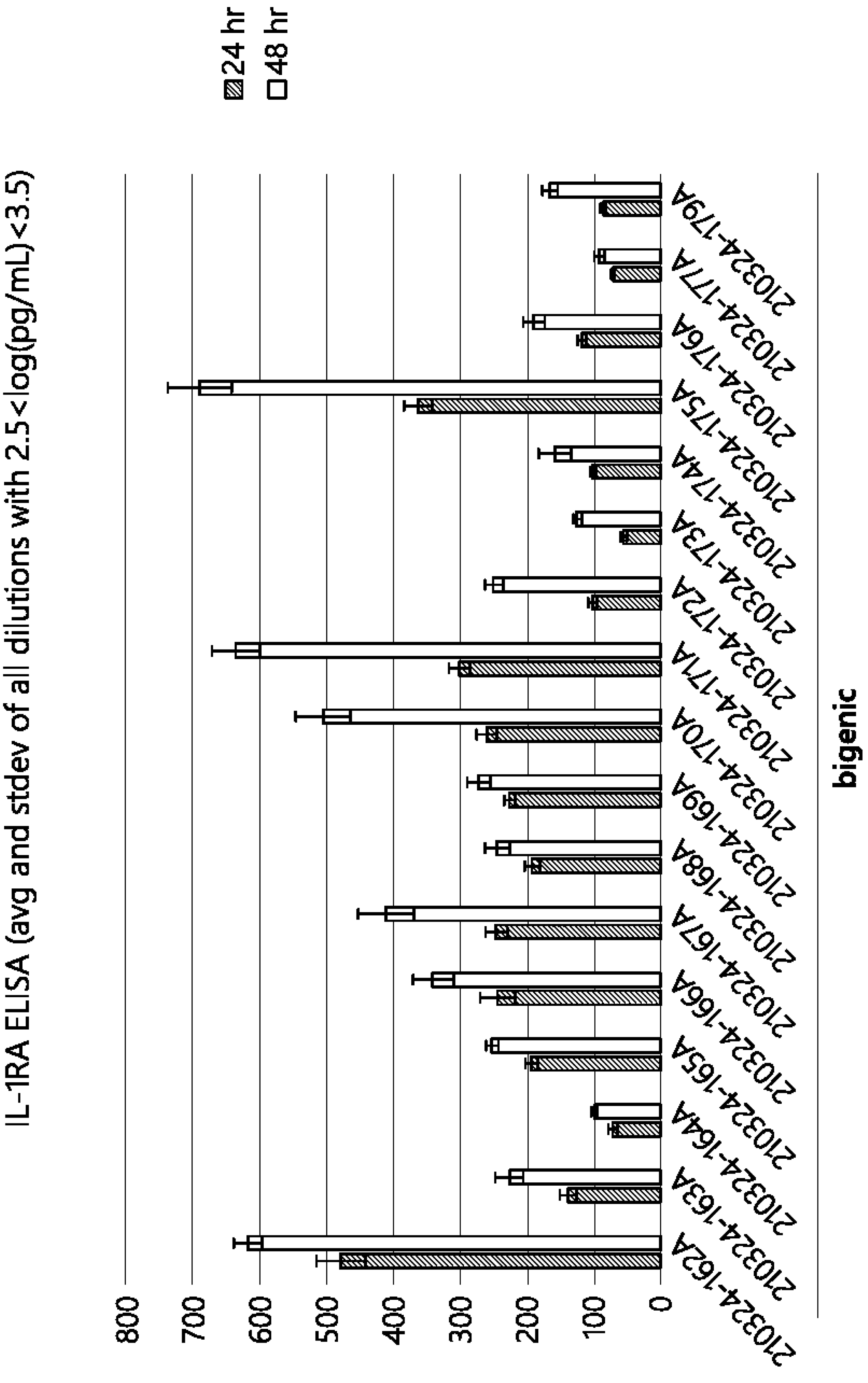
Figure 2A:
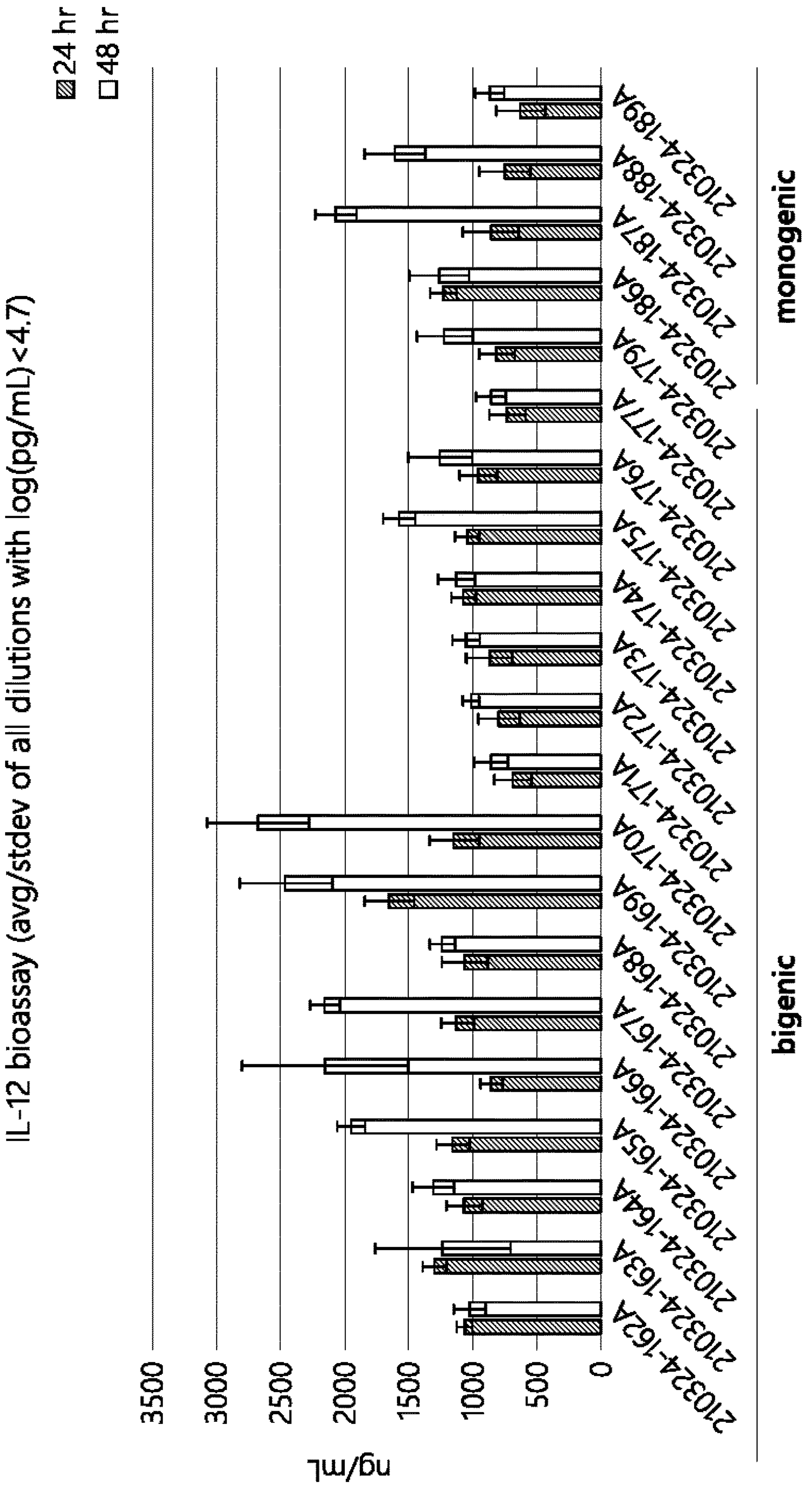
FIGS. 2A-2B are graphical representations of in vitro protein bioactivity from monogenic and multigenic constructs in VEE. Supernatants of transfected BHK-21 cells with each srRNA construct were used to measure protein bioactivity of cytokines on reporter cells expressing their cognate receptors.
Figure 2B:
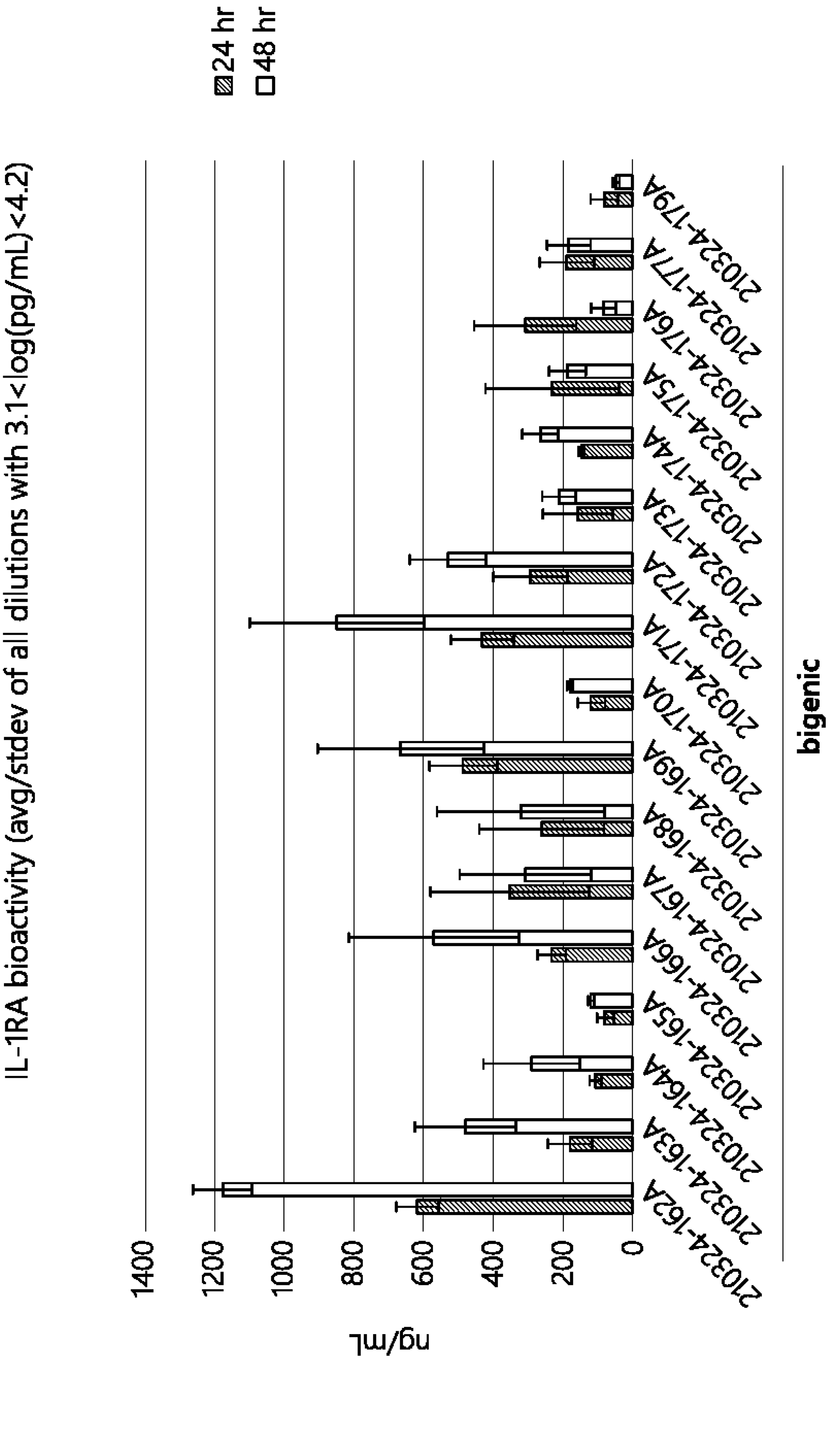

The present disclosure relates generally to nucleic acid constructs expressing variants of a p35 subunit of interleukin 12 (p35 or IL-12A), a p40 subunit of interleukin 12 (p40 or IL-12B), and an interleukin-1 receptor antagonist (IL-1RA) for the purposes of therapeutic treatment of human disease, such as, for example, cancer, immune diseases, and chronic infection. These constructs address the problem with treatment modalities, such as recombinant cytokine administration, due to the issue of dose-limiting toxicities that have been previously demonstrated. Provided herein are, inter alia, gene expression systems with superior expression potential which are suitable for expressing a coding sequence for a p35 subunit of interleukin 12 (p35 or IL-12A) or a functional variant thereof, a coding sequence for a p40 subunit of interleukin 12 (p40 or IL-12B) or functional variant thereof, and a coding sequence for an interleukin-1 receptor antagonist (IL-1RA) or a functional variant thereof, in recombinant cells. For example, some embodiments of the disclosure relate to nucleic acid constructs such as, e.g. expression constructs and vectors, containing a modified genome or srRNA of an alphavirus in which at least a portion of the nucleic acid sequence encoding the viral structural proteins of the modified alphavirus genome or srRNA has been replaced by a coding sequence for a p35 subunit of interleukin 12 (p35 or IL-12A) or a functional variant thereof, a coding sequence for a p40 subunit of interleukin 12 (p40 or IL-12B) or functional variant thereof, and a coding sequence for an interleukin-1 receptor antagonist (IL-1RA) or a functional variant thereof. Further provided are recombinant cells that are genetically engineered to include one or more of the nucleic acid molecules disclosed herein. Biomaterials and recombinant products derived from such recombinant cells are also within the scope of the application. Also provided are compositions and methods useful for eliciting cancer pharmacodynamics effect in a subject in need thereof.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

Definitions

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form “a”, “an”, and “the” include plural references unless the context clearly dictates otherwise. For example, the term “a cell” includes one or more cells, comprising mixtures thereof. “A and/or B” is used herein to include all of the following alternatives: “A”, “B”, “A or B”, and “A and B”.

The terms “administration” and “administering”, as used herein, refer to the delivery of a bioactive composition or formulation by an administration route comprising, but not limited to, intranasal, transdermal, intravenous, intra-arterial, intramuscular, intranodal, intraperitoneal, subcutaneous, intramuscular, oral, intravaginal, and topical administration, or combinations thereof. The term includes, but is not limited to, administering by a medical professional and self-administering.

The terms “cell”, “cell culture”, and “cell line” refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the original cell, cell culture, or cell line.

The term "construct" refers to a recombinant molecule, e.g., recombinant nucleic acid or polypeptide, including one or more nucleic acid sequences or amino acid sequences from heterologous sources. For example, polypeptide constructs can be chimeric polypeptide molecules in which two or more amino acid sequences of different origin are operably linked to one another in a single polypeptide construct. Similarly, nucleic acid constructs can be chimeric nucleic acid molecules in which two or more nucleic acid sequences of different origin are assembled into a single nucleic acid molecule. Representative nucleic acid constructs can include any recombinant nucleic acid molecules, linear or circular, single stranded or double stranded DNA or RNA nucleic acid molecules, derived from any source, such as a plasmid, cosmid, virus, autonomously replicating polynucleotide molecule, phage, capable of genomic integration or autonomous replication, comprising a nucleic acid molecule where one or more nucleic acid sequences have been operably linked. Two or more nucleic acid constructs can be contained within a single nucleic acid molecule, such as a single vector, or can be containing within two or more separate nucleic acid molecules, such as two or more separate vectors.

The term "operably linked", as used herein, denotes a physical or functional linkage between two or more elements, e.g., polypeptide sequences or polynucleotide sequences, which permits them to operate in their intended fashion. For example, the term "operably linked" when used in context of the nucleic acid molecules described herein or the coding sequences and promoter sequences in a nucleic acid molecule means that the coding sequences and promoter sequences are in-frame and in proper spatial and distance away to permit the effects of the respective binding by transcription factors or RNA polymerase on transcription. It should be understood that operably linked elements may be contiguous or non-contiguous (e.g., linked to one another through a linker). In the context of polypeptide constructs, "operably linked" refers to a physical linkage (e.g., directly or indirectly linked) between amino acid sequences (e.g., different segments, portions, regions, or domains) to provide for a described activity of the constructs. Operably linked segments, portions, regions, and domains of the polypeptides or nucleic acid molecules disclosed herein may be contiguous or non-contiguous (e.g., linked to one another through a linker).

The term "effective amount", "therapeutically effective amount", or "pharmaceutically effective amount" of a composition of the disclosure, e.g., nucleic acid constructs, srRNAs, recombinant cells, and/or pharmaceutical compositions, generally refers to an amount sufficient for the composition to accomplish a stated purpose relative to the absence of the composition (e.g., achieve the effect for which it is administered, stimulate an immune response, prevent or treat a disease, or reduce one or more symptoms of a disease, disorder, infection, or health condition). An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

The term "portion" as used herein refers to a fraction. With respect to a particular structure such as a polynucleotide sequence or an amino acid sequence or protein the term "portion" thereof may designate a continuous or a discontinuous fraction of said structure. For example, a portion of an amino acid sequence comprises at least 1%, at least 5%, at least 10%, at least 20%, at least 30%, at least 40%, at least 50%, at least 60%, at least 70%, at least 80%, and at least 90% of the amino acids of said amino acid sequence. In addition or alternatively, if the portion is a discontinuous fraction, said discontinuous fraction is composed of 2, 3, 4, 5, 6, 7, 8, or more parts of a structure (e.g., domains of a protein), each part being a continuous element of the structure. For example, a discontinuous fraction of an amino acid sequence may be composed of 2, 3, 4, 5, 6, 7, 8, or more, for example not more than 4 parts of said amino acid sequence, wherein each part comprises at least 1, at least 2, at least 3, at least 4, at least 5 continuous amino acids, at least 10 continuous amino acids, at least 20 continuous amino acids, or at least 30 continuous amino acids of the amino acid sequence.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. In some embodiments, the term "about" indicates the designated value ±up to 10%, up to ±5%, or up to ±1%.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI website at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated using published techniques and widely available computer programs, such as the GCS program package (Devereux et al, Nucleic Acids Res. 12:387, 1984), BLASTP, BLASTN, FASTA (Atschul et al., J Mol Biol 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

The term "pharmaceutically acceptable excipient" as used herein refers to any suitable substance that provides a pharmaceutically acceptable carrier, additive, or diluent for administration of a compound(s) of interest to a subject. As such, "pharmaceutically acceptable excipient" can encompass substances referred to as pharmaceutically acceptable diluents, pharmaceutically acceptable additives, and pharmaceutically acceptable carriers. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics and additional therapeutic agents) can also be incorporated into the compositions.

The term "recombinant" when used with reference to a cell, a nucleic acid, a protein, or a vector, indicates that the cell, nucleic acid, protein or vector has been altered or produced through human intervention such as, for example, has been modified by or is the result of laboratory methods. Thus, for example, recombinant proteins and nucleic acids include proteins and nucleic acids produced by laboratory methods. Recombinant proteins can include amino acid residues not found within the native (non-recombinant or wild-type) form of the protein or can be include amino acid residues that have been modified, e.g., labeled. The term can include any modifications to the peptide, protein, or nucleic acid sequence. Such modifications may include the following: any chemical modifications of the peptide, protein or nucleic acid sequence, including of one or more amino acids, deoxyribonucleotides, or ribonucleotides; addition, deletion, and/or substitution of one or more of amino acids in the peptide or protein; creation of a fusion protein, e.g., a fusion protein comprising an antibody fragment; and addition, deletion, and/or substitution of one or more of nucleic acids in the nucleic acid sequence. The term "recombinant" when used in reference to a cell is not intended to include naturally-occurring cells but encompass cells that have been engineered/modified to include or express a polypeptide or nucleic acid that would not be present in the cell if it was not engineered/modified.

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a health condition of interest (e.g., cancer) and/or one or more symptoms of the health condition. The subject can also be an individual who is diagnosed with a risk of the health condition of interest at the time of diagnosis or later. The term "non-human animals" includes all vertebrates, e.g., mammals, e.g., rodents, e.g., mice, non-human primates, and other mammals, such as e.g., sheep, dogs, cows, chickens, and non-mammals, such as amphibians, reptiles, etc.

It is understood that aspects and embodiments of the disclosure described herein include "comprising", "consisting", and "consisting essentially of" aspects and embodiments. As used herein, "comprising" is synonymous with "including", "containing", or "characterized by", and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In some embodiments, the genes, nucleic acid sequences, amino acid sequences, peptides, polypeptides and proteins are human. The term "gene" is also intended to include variants thereof.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Alphaviruses

Alphaviruses are small, enveloped RNA viruses with a single-stranded, positive-sense RNA genome. The alphavirus genus includes, inter alia, the Sindbis virus (SINV), the Semliki Forest virus (SFV), the Ross River virus (RRV), Venezuelan equine encephalitis virus (VEEV), and Eastern equine encephalitis virus (EEEV), which are all closely related and are able to infect various vertebrates such as mammalians, rodents, fish, avian species, and larger mammals such as humans and horses as well as invertebrates such as insects. In particular, the Sindbis and the Semliki Forest viruses have been widely studied and the life cycle, mode of replication, etc., of these viruses are well characterized.

The alphavirus genome is approximately 12 Kb long, and it consists of two open reading frames (ORFs): a 7 Kb frame encoding the nonstructural proteins (nsPs) and a 4 Kb frame encoding the structural polyprotein. The non-structural polyprotein (nsP) is cleaved into four different proteins (nsP1, nsP2, nsP3, and nsP4) which are necessary for the transcription and translation of viral mRNA inside the cytoplasm of host cells.

The nsP1 protein is an mRNA capping enzyme that possesses both guanine-7-methyltransferase (MTase) and guanylyltransferase (GTase) activities, where they direct the methylation and capping of newly synthesized viral genomic and subgenomic RNAs. The MTase motif in the N-terminal domain of nsP1 catalyzes the transfer of the methyl group from S-adenosylmethionine (AdoMet) to the N7 position of a GTP molecule (m7Gppp). GTase then binds the m7Gppp, forming a covalent link with a catalytic histidine (m7Gp-GTase) and releasing PPi. The GTase then transfers the m7Gp molecule to the 5'-diphosphate RNA to create m7GpppNp-RNA. The resulting cap structure is essential for viral mRNA translation and prevents the mRNA from being degraded by cellular 5' exonucleases. Following the N-terminal domain are features that allow the association of the nsP1 protein to cellular membranes. The presence of α-helical amphipathic loop and palmitoylation sites allow the nsP1 protein and nsP1-containing replication complex to anchor onto the plasma membrane, possibly through nsP1 interaction with the membrane's anionic phospholipids.

The nsP2 protein possesses numerous enzymatic activities and functional roles. The N-terminal region contains a helicase domain that has seven signature motif of Superfamily 1 (SF1) helicases. It functions as an RNA triphosphatase that performs the first of the viral RNA capping reactions. It also functions as a nucleotide triphosphatase (NTPase), fueling the RNA helicase activity. The C-terminal region of nsP2 contains a papain-like cysteine protease, which is responsible for processing the viral non-structural polyprotein. The protease recognizes conserved motifs within the polyprotein. This proteolytic function is highly regulated and is modulated by other domains of nsP2. The alphavirus nsP2 protein has also been described as a virulence factor responsible for the transcriptional and translational shutoff in infected host cells and the inhibition of interferon (IFN) mediated antiviral responses contributing to the controlling of translational machinery by viral factors.

The precise role(s) of alphavirus nsP3 protein in the replication complex is less clear. The nsP3 protein has three recognized domains: the N-terminal macrodomain with phosphatase activity and nucleic acid binding ability, the alphavirus unique domain (AUD) and the C-terminal hypervariable domain. It has been demonstrated that the deletion of this domain in SFV nsP3 resulted in low viral pathogenicity, suggesting its importance in viral RNA transcription regulation.

The nsP4 polymerase is the most highly conserved protein in alphaviruses, with the most divergent being >50% identical in amino acid sequence when compared with other alphaviral nsP4s. The nsP4 contains the core RNA-dependent RNA polymerase (RdRp) domain at the C-terminal end, determined to be solely responsible for the RNA synthetic properties of the viral replication complex. The RdRp participates in replicating the genomic RNA via a negative strand RNA and transcribing the 26S subgenomic RNA. The N-terminal domain is alphavirus-specific and can be partially disordered structurally.

The 5' two-thirds of the alphavirus genome encodes a number of non-structural proteins (nsPs) necessary for transcription and replication of viral RNA. These proteins are translated directly from the RNA and together with cellular proteins form the RNA-dependent RNA polymerase essential for viral genome replication and transcription of sgRNA. Four nsPs (nsP1-4) are produced as a single polyprotein constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises sgRNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The sgRNA is transcribed from the p26S subgenomic promoter present at the 3' end of the RNA sequence encoding the nsp4 protein. The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface.

Alphavirus replication has been reported to take place on membranous surfaces within the host cell. In the first step of the infectious cycle, the 5' end of the genomic RNA is translated into a polyprotein (nsP1-4) with RNA polymerase activity that produces a negative strand complementary to the genomic RNA. The sequence at the 3' end of the genomic RNA plays an important role in the initiation negative-strand synthesis, where a minimum number of adenylate residues has been identified to be essential for replication to occur. In particular, it has been previously reported that for alphavirus genomes to replicate, there must be at least 11 residues in the poly(A) tail following the 3' UTR to efficiently initiate minus-strand synthesis, and therefore replication to occur. It has also been previously reported that lengthening the poly(A) tail to 25 residues results in enhanced replication, but no further enhancement of replication was observed when the poly(A) was lengthened further to 34 residues. In addition, internal non-A residues in the poly(A) are most often deleterious to replication, which suggests that enzymatic poly(A) tailing would not benefit replicon RNA that did not exclusively contain 3' adenylate residues following the 3' UTR. It has been previously reported that there is no enhancement of minus-strand synthesis on RNA templates with greater than 25 adenylate residues in the poly(A) tail.

In a second step of replication, the negative strand is used as a template for the production of two RNAs, respectively: (1) a positive genomic RNA corresponding to the genome of the secondary viruses producing, by translation, other nsPs and acting as a genome for the virus; and (2) sgRNA encoding the structural proteins of the virus forming the infectious particles. The positive genomic RNA/sgRNA ratio is regulated by proteolytic autocleavage of the polyprotein to nsP1, nsP2, nsP3 and nsP4. In practice, the viral gene expression takes place in two phases. In a first phase, there is main synthesis of positive genomic strands and of negative strands. During the second phase, the synthesis of sgRNA is virtually exclusive, thus resulting in the production of large amount of structural protein.

Self-Replicating RNA

As will be appreciated by the skilled artisan, the term "self-replicating RNA" refers to RNA molecule that contains all of the genetic information required for directing its own self-amplification or self-replication within a permissive cell. To direct its own replication, the srRNA generally (1) encodes polymerase, replicase, or other proteins which may interact with viral or host cell-derived proteins, nucleic acids or ribonucleoproteins to catalyze the RNA amplification process; and (2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. In some embodiments of the disclosure, an alphavirus srRNA construct generally contains the following elements: 5' viral or defective-interfering RNA sequence(s) required in cis for replication, sequences coding for biologically active alphavirus non-structural proteins (e.g., nsP1, nsP2, nsP3, and nsP4), a subgenomic promoter (sg) for the subgenomic RNA (sgRNA), 3' viral sequences required in cis for replication, and optionally a polyadenylate tract (poly(A)). In some instances, a subgenomic promoter (sg) that directs expression of a heterologous sequence can be included in the srRNA construct of the disclosure.

Further, the term srRNA generally refers to a molecule of positive polarity, or "message" sense, and the srRNA may be of length different from that of any known, naturally-occurring alphavirus. In some embodiments of the present disclosure, the srRNA does not contain at least a portion of the coding sequence for one or more of the alphavirus structural proteins; and/or sequences encoding structural genes can be substituted with heterologous sequences. In those instances, where the srRNA is to be packaged into a recombinant alphavirus particle, it can contain one or more sequences, so-called packaging signals, which serve to initiate interactions with alphavirus structural proteins that lead to particle formation.

The srRNA constructs of the disclosure generally have a length of at least about 2 kb. For example, the srRNA can have a length of at least about 2 kb, at least about 3 kb, at least about 4 kb, at least about 5 kb, at least about 6 kb, at least about 7 kb, at least about 8 kb, at least about 9 kb, at least about 10 kb, at least about 11 kb, at least about 12 kb or more than 12 kb. In some embodiments, the srRNA can have a length of about 4 kb to about 20 kb, about 4 kb to about 18 kb, about 5 kb to about 16 kb, about 6 kb to about 14 kb, about 7 kb to about 12 kb, about 8 kb to about 16 kb, about 9 kb to about 14 kb, about 10 kb to about 18 kb, about 11 kb to about 16 kb, about 5 kb to about 18 kb, about 6 kb to about 20 kb, about 5 kb to about 10 kb, about 5 kb to about 8 kb, about 5 kb to about 7 kb, about 5 kb to about 6 kb, about 6 kb to about 12 kb, about 6 kb to about 11 kb, about 6 Kb to about 10 kb, about 6 Kb to about 9 Kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb. In some embodiments, the srRNA can have a length of about 6 kb to about 14 kb. In some embodiments, the srRNA can have a length of about 6 kb to about 16 kb.

IL-12

IL-12 is a heterodimer with a molecular weight of 70 kDa consisting of a heavy (p40) and a light (p35) chain subunit, which are covalently linked by disulfide bonds. While p40 is produced in abundance by phagocytic cells, p35 is ubiquitously and constitutively expressed only at low levels and is thought to require p40 co-expression for secretion of the biologically active cytokine (Babik J M, Adams E, Tone Y, Fairchild P J, Tone M, Waldmann H. Expression of murine IL-12 is regulated by translational control of the p35 subunit. *J Immunol* 1999; 162: 4069-4078).

IL-12 signals through a receptor complex of IL-12Rβ1 and IL-12Rβ2 expressed on NK cells and T cells. Dimerization of the IL-12 receptor induces activation of receptor associated Janus Kinase (JAK) molecules which phosphorylate each other as well as residues on the intracellular domain of IL-12Rβ2 which serve as docking sites for the SH2 containing signal transducer and activator of transcription 4 (STAT4). Receptor associated STAT4 proteins are then phosphorylated prior to translocating to the nucleus where they promote the expression of IFNγ and the polarization of CD4+ T cells towards a T helper 1 (Th1) phenotype. Given the similarities between immunity to intracellular pathogens and cancer, therapeutic approaches that stimulate Th1 responses, either indirectly through selection of vaccine adjuvants and epitopes, or directly, through administration of IL-12, have been explored in the context of cancer immunotherapy. Despite promise in pre-clinical models, therapeutic efficacy of IL-12 administration has been limited due to toxicity associated with NK cell mediated production of IFNγ.

IL-1RA

Interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1α and IL-1β can be generated by macrophages, monocytes, and dendritic cells, and can be part of the inflammatory response against infection.

The mode of action of IL-1 cytokines can be mediated by interleukin-1 receptor antagonist protein (IL-1RA; also known as "IRAP") encoded by the IL1RN gene. IL-1RA binds to the same receptor on the cell surface as IL-1α and IL-1β, and thus prevents these cytokines from sending a signal to that cell. IL-1RA is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1RA is stimulated by several substances including adherent immunoglobulin G (IgG), other cytokines, and bacterial or viral components. IL-1RA is an important natural anti-inflammatory protein in arthritis, colitis, and granulomatous pulmonary disease.

Compositions of the Disclosure

As described in greater detail below, one aspect of the present disclosure relates to nucleic acid constructs containing sequences that encode a modified alphavirus genome or srRNA where at least a portion of the nucleic acid sequence encoding the viral structural proteins of the modified alphavirus genome or srRNA has been replaced by an coding sequence for a polypeptide construct comprising a) a coding sequence for a p35 subunit of interleukin 12 (p35 or IL-12A) or a functional variant thereof, b) a coding sequence for a p40 subunit of interleukin 12 (p40 or IL-12B) or functional variant thereof, and c) a coding sequence for an interleukin-1 receptor antagonist (IL-1RA) or a functional variant thereof. Also provided are recombinant cells and cell cultures that have been engineered to include a nucleic acid construct as disclosed herein.

Nucleic Acid Constructs

As described in greater detail below, one aspect of the present disclosure relates to nucleic acid constructs including a nucleic acid sequence encoding a modified alphavirus genome or srRNA where at least a portion of the nucleic acid sequence encoding the viral structural proteins of the modified alphavirus genome or srRNA has been replaced by an coding sequence for a polypeptide construct comprising a) a coding sequence for a p35 subunit of interleukin 12 (p35 or IL-12A) or a functional variant thereof, b) a coding sequence for a p40 subunit of interleukin 12 (p40 or IL-12B) or functional variant thereof, and c) a coding sequence for an interleukin-1 receptor antagonist (IL-1RA) or a functional variant thereof. In some embodiments, the sequence encoding a srRNA construct can be operably linked, e.g., placed under the control of elements required for expression (e.g., promoter sequences), which allow expression of the srRNA construct in a host cell, in a subject, or in an ex-vivo cell-free expression system.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be of any length, including for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Non-limiting exemplary embodiments of the methods of the disclosure can include one or more of the following features. In some embodiments, the alphavirus srRNA vector is devoid of at least a portion of the nucleic acid sequence encoding one or more of the viral structural proteins CP, E1, E2, E3, and 6K of the alphavirus srRNA vector. In some embodiments, the alphavirus srRNA vector is devoid of a portion of or the entire sequence encoding CP. In some embodiments, the alphavirus srRNA vector is devoid of a portion of or the entire sequence encoding E1. In some embodiments, the alphavirus srRNA vector is devoid of a portion of or the entire sequence encoding E2. In some embodiments, the alphavirus srRNA vector is devoid of a portion of or the entire sequence encoding E3. In some embodiments, the alphavirus srRNA vector is devoid of a portion of or the entire sequence encoding 6K. In some embodiments, the alphavirus srRNA vector is devoid of a portion of or the entire sequence encoding a combination of CP, E1, E2, E3, and 6K. In some embodiments of the disclosure, the coding sequence for nonstructural proteins nsP1, nsP2, nsP3, and nsP4 of the alphavirus srRNA vector is present, however at least a portion of or the entire sequence encoding one or more structural proteins (e.g., CP, E1, E2, E3, and 6K) of the alphavirus srRNA vector is absent.

In some embodiments, the alphavirus srRNA vector is devoid of a substantial portion of the nucleic acid sequence encoding one or more viral structural proteins. The skilled artisan will understand that a substantial portion of a nucleic acid sequence encoding a viral structural polypeptide can include enough of the nucleic acid sequence encoding the viral structural polypeptide to afford putative identification of that polypeptide, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993). Accordingly, a substantial portion of a nucleotide sequence comprises enough of the sequence to afford specific identification and/or isolation of a nucleic acid fragment comprising the sequence. For example, a substantial portion of a nucleic acid sequence can include at least about 20%, for example, about 30%, about 40%, about 50%, about 60%, about 70%, about 80%, about 90%, about 95% of the full length nucleic acid sequence.

In some embodiments, the alphavirus srRNA vector is devoid of the entire sequence encoding viral structural proteins, e.g., the alphavirus srRNA vector includes no nucleic acid sequence encoding the viral structural proteins.

The nucleic acid constructs of the disclosure further include a coding sequence for a polypeptide construct that replaces at least a portion of the nucleic acid sequence encoding the viral structural proteins of the modified alphavirus genome or srRNA. In principle, the nucleic acid constructs disclosed herein can generally include any number of coding sequences for a polypeptide construct. In some embodiments, the nucleic acid constructs disclosed herein can include at least one, at least two, at least three, at least four, at least five, or at least six coding sequences for polypeptide constructs. A coding sequence for a polypeptide construct can be a construct of genetic material that contains coding sequences and enough regulatory information to direct proper transcription and/or translation of the coding sequences in a cell, in vivo and/or ex vivo. The coding sequence for a polypeptide construct can be inserted into a vector for targeting to a desired host cell and/or into a subject. Accordingly, in some embodiments, the term "coding sequence for a polypeptide construct" can be used interchangeably with the term "expression construct." In some embodiments, a coding sequence for a polypeptide construct can be a nucleic acid construct that includes a gene encoding a protein or functional RNA operably linked to regulatory elements such as, for example, a promoter and/or a termination signal, and optionally, any or a combination of other nucleic acid sequences that affect the transcription or translation of the gene.

The nucleic acid constructs described herein include a coding sequence for the p35 subunit of interleukin 12 (p35 or IL-12A) or a functional variant thereof, a coding sequence for a p40 subunit of interleukin 12 (p40 or IL-12B) or functional variant thereof, and a coding sequence for an interleukin-1 receptor antagonist (IL-1RA) or a functional variant thereof, which encode polypeptides that are able to elicit a pharmacodynamics effect in a subject. The functional variants of IL-12A, IL-12B, and IL-1RA can encompass coding sequences for polypeptides having an amino acid sequence that is the same or essentially the same as that of the reference protein (e.g., IL-12A, IL-12B, and IL-1RA) except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein. The terms "variant", when used in reference to a nucleic acid sequence, refer to a nucleic acid sequence that differs by one or more nucleotides from another, usually related nucleotide acid sequence. As such, the term "variant" can refer to a change of one or more nucleotides of a reference nucleic acid which includes the insertion of one or more new nucleotides, deletion of one or more nucleotides, and substitution of one or more existing nucleotides. A variant can also include a point mutation, multiple mutation, single nucleotide polymorphism (SNP), deletion, insertion, and translocation. Thus, variants of the coding sequences described herein include nucleic acids that encode polypeptides that can be, for example, full length, mutated, truncated, inactivated, peptide/epitopes or combinations thereof of IL-12A, IL-12B, and IL-1RA.

The full-length amino acid sequence of the human IL-12 p35 subunit is set forth in SEQ ID NO: 1 as follows:

```
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS
```

Alternatively, the full-length amino acid sequence of the human IL-12 p35 subunit along with its signal sequence is set forth in SEQ ID NO: 2 as follows:

```
MCPARSLLLVATLVLLDHLSLARNLPVATPDPGMFPCLHHSQNLLRAVSN

MLQKARQTLEFYPCTSEEIDHEDITKDKTSTVEACLPLELTKNESCLNSR

ETSFITNGSCLASRKTSFMMALCLSSIYEDLKMYQVEFKTMNAKLLMDPK
```

-continued

```
RQIFLDQNMLAVIDELMQALNFNSETVPQKSSLEEPDFYKTKIKLCILLH

AFRIRAVTIDRVMSYLNAS
```

In some embodiments, the coding sequence for the IL-12 p35 subunit in the nucleic acid constructs described herein encodes the amino acid sequence of SEQ ID NO: 1 or SEQ ID NO: 2. In some embodiments, the nucleic acid constructs of the disclosure include a nucleic acid sequence encoding an IL-12 p35 subunit having at least 80%, at least 85%, at least 90%, at least 95%, at least 96%, at least 97%, at least 98%, at least 99%, or 100% sequence identity to an amino acid sequence of SEQ ID NO: 1 or SEQ ID NO: 2. In some embodiments, the coding sequence for the IL-12 p35 subunit encodes smaller portions of the amino acid sequence of SEQ ID NO: 1 or SEQ ID NO: 2. These smaller portions can include at least 8, 10, 12, 14, 16, 18, 20, 30 or more amino acids of SEQ ID NO: 1 or SEQ ID NO: 2.

In some embodiments, the coding sequence for a polypeptide construct in the nucleic acids described herein encodes IL-12 p35 subunit functional variants.

As described supra, the nucleic acid constructs described herein also include coding sequences for IL-12 p40 subunit or a functional variant thereof.

The full-length amino acid sequence of the human IL-12 p40 subunit is set forth in SEQ ID NO: 3 as follows:

```
IWELKKDVYWELDWYPDAPGEMWLTCDTPEEDGITWTLDQSSEVLGSGKT

LTIQVKEFGDAGQYTCHKGGEVLSHSLLLLHKKEDGIWSTDILKDQKEPN

KTFLRCEAKNYSGRFTCWLTTISTDLTFSVKSSRGSSDPQGVTCGAATLS

AERVRGDNKEYEYSVECQEDSACPAAEESLPIEVMVDAVHKLKYENYTSS

FFIRDIIPDPPKNLDLfPLiWS
```

Alternatively, the full-length amino acid sequence of the human IL-12 p40 subunit along with its signal sequence is set forth in SEQ ID NO: 4 as follows:

```
MCHQQLVISWFSLVFLASPLVAIWELKKDVYVVELDWYPDAPGEMVVLTC

DTPEEDGITWTLDQSSEVLGSGKTLTIQVKEFGDAGQYTCHKGGEVLSHS

LLLLHKKEDGIWSTDILKDQKEPKNKTFLRCEAKNYSGRFTCWWLTTIST

DLTFSVKSSRGSSDPQGVTCGAATLSAERVRGDNKEYEYSVECQEDSACP

AAEESLPIEVMVDAVHKLKYENYTSSFFIRDIIKPDPPKNLQLKPLKNSR

QVEVSWEYPDTWSTPHSYFSLTFCVQVQGKSKREKKDRVFTDKTSATVIC

RKNASISVRAQDRYYSSSWSEWASVPCS
```

In some embodiments, the coding sequence for the human IL-12 p40 subunit in the nucleic acid constructs described herein encodes the amino acid sequence of SEQ ID NO: 3 or SEQ ID NO: 4. In some embodiments, the nucleic acid constructs of the disclosure include a nucleic acid sequence encoding the human IL-12 p40 subunit having at least 80%, at least 85%, at least 90%, at least 95%, at least 96%, at least 97%, at least 98%, at least 99%, or 100% sequence identity to an amino acid sequence of SEQ ID NO: 3 or SEQ ID NO: 4. In some embodiments, the coding sequence for the human IL-12 p40 subunit encodes smaller portions of the amino acid sequence of SEQ ID NO: 3 or SEQ ID NO: 4. These smaller portions can include at least 8, 10, 12, 14, 16, 18, 20 or more amino acids of SEQ ID NO: 3 or SEQ ID NO: 4.

In some embodiments, the coding sequence for a polypeptide construct in the nucleic acids described herein encode an IL-12 p40 subunit functional variant.

As described supra, the nucleic acid constructs described herein also include coding sequences for IL-RA or a functional variant thereof.

In some embodiments, the coding sequence for a polypeptide construct in the nucleic acids described herein encode one or more regions of IL-1RA transcripts 1, 2, 3, or 4, intracellular IL-1RA (icIL-1Ra), or their corresponding polypeptide isoforms. Alternatively, compositions comprise the entirety of IL-1RA transcripts 1, 2, 3, or 4, intracellular IL-1RA (icIL-1Ra), or their corresponding polypeptide isoforms. Compositions comprising any form of human IL-1Ra, or fragments thereof, inhibit the function of IL-1R1.

The amino acid sequence for human IL-1RA encoded by IL1RN transcript 1 and set forth in SEQ ID NO: 5 is as follows:

```
MEICRGLRSHLITLLLFLFHSETICRPSGRKSSKMQAFRIWDVNQKTFYL
RNNQLVAGYLQGPNVNLEEKIDVVPIEPHALFLGIHGGKMCLSCVKSGDE
TRLQLEAVNITDLSENRKQDKRFAFIRSDSGPTTSFESAACPGWFLCTAM
EADQPVSLTNMPDEGVMVTKFYFQEDE.
```

In some embodiments, the nucleic acid constructs of the disclosure include a nucleic acid sequence encoding and IL-1RA variant having at least 80%, at least 85%, at least 90%, at least 95%, at least 96%, at least 97%, at least 98%, at least 99%, or 100% sequence identity to an amino acid sequence of SEQ ID NO: 5.

The amino acid sequence for human IL-1RA encoded by IL1RN transcript 2 and set forth in SEQ ID NO: 6 is as follows (NCBI Accession No. NM_173841):

```
MALADLYEEGGGGGGEGEDNADSKETICRPSGRKSSKMQAFRIWDVNQKT
FYLRNNQLVAGYLQGPNVNLEEKIDVVPIEPHALFLGIHGGKMCLSCVKS
GDETRLQLEAVNITDLSENRKQDKRFAFIRSDSGPTTSFESAACPGWFLC
TAMEADQPVSLTNMPDEGVMVTKFYFQEDE
```

In some embodiments, the nucleic acid constructs of the disclosure include a nucleic acid sequence encoding and IL-1RA variant having at least 80%, at least 85%, at least 90%, at least 95%, at least 96%, at least 97%, at least 98%, at least 99%, or 100% sequence identity to an amino acid sequence of SEQ ID NO: 6.

The amino acid sequence for human IL-1RA encoded by IL1RN transcript 3 and set forth in SEQ ID NO: 7 is as follows (NCBI Accession No. NM_000577):

```
MALETICRPSGRKSSKMQAFRIWDVNQKTFYLRNNQLVAGYLQGPNVNLE
EKIDVVPIEPHALFLGIHGGKMCLSCVKSGDETRLQLEAVNITDLSENRK
QDKRFAFIRSDSGPTTSFESAACPGWFLCTAMEADQPVSLTNMPDEGVMV
TKFYFQEDE
```

In some embodiments, the nucleic acid constructs of the disclosure include a nucleic acid sequence encoding and IL-1RA variant having at least 80%, at least 85%, at least 90%, at least 95%, at least 96%, at least 97%, at least 98%, at least 99%, or 100% sequence identity to an amino acid sequence of SEQ ID NO: 7.

The amino acid sequence for human IL-1RA encoded by IL1RN transcript 4 and set forth in SEQ ID NO: 8 is as follows (NCBI Accession No. NM_173843):

```
MQAFRIWDVNQKTFYLRNNQLVAGYLQGPNVNLEEKIDVVPIEPHALFLG
IHGGKMCLSCVKSGDETRLQLEAVNITDLSENRKQDKRFAFIRSDSGPTT
SFESAACPGWFLCTAMEADQPVSLTNMPDEGVMVTKFYFQEDE
```

In some embodiments, the nucleic acid constructs of the disclosure include a nucleic acid sequence encoding and IL-1RA variant having at least 80%, at least 85%, at least 90%, at least 95%, at least 96%, at least 97%, at least 98%, at least 99%, or 100% sequence identity to an amino acid sequence of SEQ ID NO: 8.

The amino acid sequence for human intracellular IL-1RA, icIL-1Ra set forth in SEQ ID NO: 9 is as follows (NCBI Accession No. M55646):

```
MALETICRPSGRKSSKMQAFRIWDVNQKTFYLRNNQLVAGYLQGPNVNLE
EKIDVVPIEPHALFLGIHGGKMCLSCVKSGDETRLQLEAVNITDLSENRK
QDKRFAFIRSDSGPTTSFESAACPGWFLCTAMEADQPVSLTNMPDEGVM
VTKFYFQEDE.
```

In some embodiments, the nucleic acid constructs of the disclosure include a nucleic acid sequence encoding an IL-1RA variant having at least 80%, at least 85%, at least 90%, at least 95%, at least 96%, at least 97%, at least 98%, at least 99%, or 100% sequence identity to an amino acid sequence of SEQ ID NO: 9.

In some embodiments, the coding sequence for the IL-12 p35 subunit or functional variant thereof, IL-12 p40 subunit or functional variant thereof, and IL-1RA or functional variant thereof includes a coding sequence for a single polypeptide (e.g., monogenic). In some embodiments, the coding sequence for the IL-12 p35 subunit or functional variant thereof, IL-12 p40 subunit or functional variant thereof, and IL-1RA or functional variant thereof includes coding sequences for a plurality of polypeptides, e.g., multigenic (e.g., bigenic or trigenic). In some embodiments, each of the coding sequences of IL-12 p35 subunit or functional variant thereof, IL-12 p40 subunit or functional variant thereof, and IL-1RA or functional variant thereof is operably linked to a separate promoter sequence. In some embodiments, the coding sequences of IL-12 p35 subunit or functional variant thereof, IL-12 p40 subunit or functional variant thereof, and IL-1RA or functional variant thereof are operably linked to one another within a single open reading frame (e.g., in a polycistronic ORF). In some embodiments, the coding sequence of the polycistronic ORF is operably linked to a promoter sequence. In some embodiments, at least one of the promoter sequences is a subgenomic (sg) promoter. In some embodiments, the sg promoter is a 26S genomic promoter.

In some embodiments, the coding sequences for IL-12 p35 subunit or functional variant thereof, IL-12 p40 subunit or functional variant thereof, and IL-1RA or functional variant thereof, can be linked to one another directly or indirectly (e.g., via one or more connector sequences). For example, in some embodiments, the coding sequences can be directly linked to one another, e.g., adjacently to one another. In some embodiments, at least two (e.g., 2, 3, 4, or 5) of the coding sequences are operably linked to one another by one or more connector sequences. In some embodiments, the length and amino acid composition of the connector sequences can be optimized to vary the orientation, flexibility, and/or proximity of the polypeptides relative to one another to achieve a desired activity or property of the encoded protein. In some embodiments, a connector sequence of the plurality of connector sequences includes one or more coding sequences for autoproteolytic peptide sequences. Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term “autoproteolytic peptide” refers to a “self-cleaving” peptide that possesses autoproteolytic activity and is capable of cleaving itself from a larger polypeptide moiety. First identified in the foot-and-mouth disease virus (FMDV), a member of the picornavirus group, several autoproteolytic peptides have been subsequently identified such as, for example, “2A like” peptides from equine rhinitis A virus (E2A), porcine teschovirus-1 (P2A) and Thosea asigna virus (T2A), and their activities in proteolytic cleavage have been shown in various ex vitro, in vitro, ex vivo, and in vivo eukaryotic systems. As such, the concept of autoproteolytic peptides is available to one of skill in the art with many naturally-occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoproteolytic peptides suitable for the compositions and methods of the present disclosure include one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequences for IL-12 p35 subunit or functional variant thereof, IL-12 p40 subunit or functional variant thereof, and IL-1RA or functional variant thereof are operably linked to one another by a coding sequence for one or more an internal ribosomal entry sites (IRES). An IRES or “internal ribosome entry site” is a sequence located between polycistronic genes that permits the production of the expression product originating from the second gene by internal initiation of the translation of the dicistronic mRNA. It promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. In some embodiments, the IRES can be a viral IRES, a cellular IRES, or an artificial IRES. Examples of IRES generally employed by those of skill in the art include those described in U.S. Pat. No. 6,692,736. In some embodiments, the IRES is selected from a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, and a c-myc IRES, In some embodiments, the IRES is obtainable from EMCV.

One of skill in the art will appreciate that different configurations of coding sequences for IL-12 p35 subunit or functional variant thereof, IL-12 p40 subunit or functional variant thereof, and IL-1RA or functional variant thereof, the sequence encoding the autoproteolytic peptide, or an IRES can be employed as long as expression of IL-12 p35 subunit or functional variant thereof, IL-12 p40 subunit or functional variant thereof, and IL-1RA or functional variant thereof is adequately maintained. These sequences will typically be configured so that the polypeptide encoded by the gene of interest can be released from the protease and other sequence after cleavage by the autoprotease.

The term “operably linked”, as used herein, denotes a functional linkage between two or more sequences. For example, an operably linkage between a polynucleotide of interest and a regulatory sequence (for example, a promoter) is functional link that allows for expression of the polynucleotide of interest. In this sense, the term “operably linked” refers to the positioning of a regulatory region and a coding sequence to be transcribed so that the regulatory region is effective for regulating transcription or translation of the coding sequence of interest. In some embodiments disclosed herein, the term “operably linked” denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The basic techniques for operably linking two or more sequences of DNA together are familiar to one of ordinary skill in the art, and such methods have been described in many books for standard molecular biological manipulation (see, for example, Maniatis et al., “Molecular Cloning: A Laboratory Manual” 2nd ed. Cold Spring Harbor Laboratory Press, Cold Spring Harbor, N.Y.; and Gibson et al., Nature Methods 6:343-45, 2009).

As shown in FIGS. 1A-1B and 2A-2B, IL-12 and IL-1RA protein expression and bioactivity were measured from different bigenic constructs having different ordinalities of genes. Exemplary configurations of the nucleic acid constructs described herein are shown in Table 1 below.

TABLE 1

| Construct ID | Alphavirus | Ordinality of Genes |
|---|---|---|
| pRB-162 | VEE | P35-P2A-p40-IRES-IL1RN |
| pRB-163 | VEE | P35-IRES-p40-P2A-IL1RN |
| pRB-164 | VEE | P35-P2A-p40-P2A-IL1RN |
| pRB-165 | VEE | IL1RN-P2A-p35-IRES-p40 |
| pRB-166 | VEE | IL1RN-IRES-p35-P2A-p40 |
| pRB-167 | VEE | IL1RN-P2A-p35-P2A-p40 |
| pRB-168 | VEE | IL1RN-P2A-p40-IRES-p35 |
| pRB-169 | VEE | IL1RN-IRES-p40-P2A-p35 |
| pRB-170 | VEE | IL1RN-P2A-p40-P2A-p35 |
| pRB-171 | VEE | P40-P2A-p35-IRES-IL1RN |
| pRB-172 | VEE | P40-IRES-p35-P2A-IL1RN |
| pRB-173 | VEE | P40-P2A-p35-P2A-IL1RN |
| pRB-174 | VEE | P35-P2A-IL1RN-IRES-p40 |
| pRB-175 | VEE | P35-IRES-IL1RN-P2A-p40 |
| pRB-176 | VEE | P35-P2A-IL1RN-P2A-p40 |
| pRB-177 | VEE | P40-P2A-IL1RN-IRES-p35 |
| pRB-179 | VEE | P40-P2A-IL1RN-P2A-p35 |
| pRB-299 | VEE | p35-P2A-p40-IRES-IL1RN |
| pRB-303 | CHIK.S27 | p35-P2A-p40-IRES-IL1RN |
| pRB-301 | CHIK.DRDE | p35-P2A-p40-IRES-IL1RN |

TABLE 1-continued

| Construct ID | Alphavirus | Ordinality of Genes |
|---|---|---|
| pRB-309 | SIND.G. | p35-P2A-p40-IRES-IL1RN |
| pRB-307 | SIND.AR86 | p35-P2A-p40-IRES-IL1RN |
| pRB-305 | EEE | p35-P2A-p40-IRES-IL1RN |
| pRB-300 | VEE | IL1RN-IRES-p40-P2A-p35 |
| pRB-304 | CHIK.S27 | IL1RN-IRES-p40-P2A-p35 |
| pRB-302 | CHIK.DRDE | IL1RN-IRES-p40-P2A-p35 |
| pRB-310 | SIND.G | IL1RN-IRES-p40-P2A-p35 |
| pRB-308 | SIND.AR86 | IL1RN-IRES-p40-P2A-p35 |
| pRB-306 | EEE | IL1RN-IRES-p40-P2A-p35 |

In some embodiments, the ordinality of the nucleic acid construct is selected from the group consisting of pRB-299 and pRB-306.

In some embodiments, the polypeptide construct comprises, in N-terminus to C-terminus direction: a) an IL-12A polypeptide, an IL-12B polypeptide, and an IL-1RA polypeptide; or; b) an IL-1RA polypeptide, an IL-12B polypeptide, and an IL-12A polypeptide; wherein the IL-12A, IL-12B, and IL-1RA polypeptides are operably linked to one another by one or more autoproteolytic cleavage sequences or internal ribosomal entry sites.

In some embodiments, nucleic acid sequence has at least 80%, at least 85%, at least 90%, at least 95%, at least 96%, at least 97%, at least 98%, at least 99%, or 100% sequence identity to a nucleic acid sequence of SEQ ID NO: 10.

In some embodiments, the coding sequence of IL-12 p35, IL-12 p40, and IL-1RA is redesigned and/or optimized for a desired property, such as increased stability, potency, and expression (e.g., translation efficiency), which in turns can maximize the impact of producing, delivering, and administering biotherapeutic. For example, in some embodiments, the coding sequence is optimized for expression at a level higher than the expression level of a reference coding sequence. With respect to sequence-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the nucleic acid constructs of the present disclosure may also have any base sequence that has been changed from any polynucleotide sequence disclosed herein by substitution in accordance with degeneracy of the genetic code. References describing codon usage are readily publicly available. In some embodiments, polynucleotide sequence variants can be produced for a variety of reasons, e.g., to optimize expression for a particular host (e.g., changing codon usage in the alphavirus mRNA to those preferred by other organisms such as human, non-human primates, hamster, mice, or monkey). Accordingly, in some embodiments, the coding sequence is optimized for expression in a target host cell through the use of codons optimized for expression. The techniques for the construction of synthetic nucleic acid sequences encoding genes using preferred codons optimal for host cell expression may be determined by computational methods analyzing the commonality of codon usage for encoding native proteins of the host cell genome and their relative abundance by techniques well known in the art. The codon usage database may be used for generation of codon optimized sequences in mammalian cell environments. Furthermore, a variety of software tools are available to convert sequences from one organism to the optimal codon usage for a different host organism such as the JCat Codon Optimization Tool (www.jcat.de), Integrated DNA Technologies (IDT) Codon Optimization Tool or the Optimizer online codon optimization tool. Such synthetic sequences may be constructed by techniques known in the art for the construction of synthetic nucleic acid molecules and may be obtained from a variety of commercial vendors.

In some embodiments, the coding sequence is optimized for enhanced RNA stability and/or expression. The stability of RNA generally relates to the "half-life" of RNA. "Half-life" relates to the period of time which is needed to eliminate half of the activity, amount, or number of molecules. In the context of the present disclosure, the half-life of an RNA is indicative for the stability of said RNA. The half-life of RNA may influence the "duration of expression" of the RNA. Additional information regarding principles, strategies, and methods for use in enhancing RNA stability can be found at, for example, Leppek K. et al., *Combinatorial optimization of mRNA structure, stability, and translation for RNA-based therapeutics*. bioRxiv. (Preprint). Mar. 30, 2021. doi: 10.1101/2021.03.29.437587.

Recombinant Cells

The nucleic acid constructs of the present disclosure can be introduced into a host cell to produce a recombinant cell containing the nucleic acid molecule. Accordingly, prokaryotic or eukaryotic cells that contain a nucleic acid construct encoding a modified alphavirus genome as described herein are also features of the disclosure. In a related aspect, some embodiments disclosed herein relate to methods of transforming a cell which includes introducing into a host cell, such as an animal cell, a nucleic acid construct as provided herein, and then selecting or screening for a transformed cell. Introduction of the nucleic acid constructs of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, direct micro-injection, nanoparticle-mediated nucleic acid delivery, and the like.

In one aspect, some embodiments of the disclosure relate to recombinant cells, for example, recombinant animal cells that include a nucleic acid construct described herein. The nucleic acid construct can be stably integrated in the host genome, or can be episomally replicating, or present in the recombinant host cell as a mini-circle expression vector for a stable or transient expression. Accordingly, in some embodiments of the disclosure, the nucleic acid construct is maintained and replicated in the recombinant host cell as an episomal unit. In some embodiments, the nucleic acid construct is stably integrated into the genome of the recombinant cell. Stable integration can be completed using classical random genomic recombination techniques or with more precise genome editing techniques such as using guide RNA directed CRISPR/Cas9 or TALEN genome editing. In some embodiments, the nucleic acid construct present in the recombinant host cell as a mini-circle expression vector for a stable or transient expression.

In some embodiments, the recombinant cell is a prokaryotic cell, such as the bacterium *E. coli*, or a eukaryotic cell, such as an insect cell (e.g., a mosquito cell or a Sf21 cell), or mammalian cells (e.g., COS cells, NIH 3T3 cells, or HeLa cells). In some embodiments, the cell is in vivo. In some embodiments, the cell is ex vivo. In some embodiments, the cell is in vitro. In some embodiments, the recombinant cell is a eukaryotic cell. In some embodiments, the recombinant cell is an animal cell. In some embodiments, the animal cell is a vertebrate animal cell or an invertebrate animal cell. In some embodiments, the recombinant cell is a mammalian cell. In some embodiments, the recombinant cell is selected from the group consisting of a monkey kidney CV1 cell transformed by SV40 (COS-7), a human embryonic kidney cell (e.g., HEK 293 or HEK 293 cell), a baby hamster kidney cell (BHK), a mouse sertoli cell (e.g., TM4 cells), a monkey kidney cell (CV1), a human cervical carcinoma cell (HeLa), a canine kidney cell (MDCK), a buffalo rat liver cell (BRL 3A), a human lung cell (W138), a human liver cell (Hep G2), a mouse mammary tumor (MMT 060562), a TRI cell, a FS4 cell, a Chinese hamster ovary cell (CHO cell), an African green monkey kidney cell (Vero cell), a human A549 cell, a human cervix cell, a human CHME5 cell, a human PER.C6 cell, a NS0 murine myeloma cell, a human epidermoid larynx cell, a human fibroblast cell, a human HUH-7 cell, a human MRC-5 cell, a human muscle cell, a human endothelial cell, a human astrocyte cell, a human macrophage cell, a human RAW 264.7 cell, a mouse 3T3 cell, a mouse L929 cell, a mouse connective tissue cell, a mouse muscle cell, and a rabbit kidney cell.

In some embodiments, the recombinant cell is an insect cell, e.g., cell of an insect cell line. In some embodiments, the recombinant cell is a Sf21 cell. Additional suitable insect cell lines include, but are not limited to, cell lines established from insect orders Diptera, Lepidoptera and Hemiptera, and can be derived from different tissue sources. In some embodiments, the recombinant cell is a cell of a lepidopteran insect cell line. In the past few decades, the availability of lepidopteran insect cell lines has increased at about 50 lines per decade. More information regarding available lepidopteran insect cell lines can be found in, e.g., Lynn D. E., *Available lepidopteran insect cell lines*. Methods Mol Biol. 2007; 388:117-38, which is herein incorporated by reference. In some embodiments, the recombinant cell is a mosquito cell, e.g., a cell of mosquito species within *Anopheles* (An.), *Culex* (Cx.) and *Aedes* (*Stegomyia*) (Ae.) genera. Exemplary mosquito cell lines suitable for the compositions and methods described herein include cell lines from the following mosquito species: *Aedes aegypti, Aedes albopictus, Aedes pseudoscutellaris, Aedes triseriatus, Aedes vexans, Anopheles gambiae, Anopheles stephensi, Anopheles albimanus, Culex quinquefasciatus, Culex theileri, Culex tritaeniorhynchus, Culex bitaeniorhynchus*, and *Toxorhynchites amboinensis*. Suitable mosquito cell lines include, but are not limited to, CCL-125, Aag-2, RML-12, C6/26, C6/36, C7-10, AP-61, A.t. GRIP-1, A.t. GRIP-2, UM-AVE1, Mos.55, Sua1B, 4a-3B, Mos.43, MSQ43, and LSB-AA695BB. In some embodiments, the mosquito cell is a cell of a C6/26 cell line.

In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

The recombinant polypeptides produced by the method disclosed herein are also within the scope of the disclosure.

Non-limiting exemplary embodiments of the disclosed methods for producing a recombinant polypeptide can include one or more of the following features. In some embodiments, the methods for producing a recombinant polypeptide of the disclosure further include isolating and/or purifying the produced polypeptide. In some embodiments, the methods for producing a polypeptide of the disclosure further include structurally modifying the produced polypeptide to increase half-life.

Pharmaceutical Compositions

The nucleic acid constructs, recombinant cells, recombinant polypeptides of the disclosure can be incorporated into compositions, including pharmaceutical compositions. Such compositions generally include one or more of the nucleic acid constructs, recombinant cells, recombinant polypeptides described and provided herein, and a pharmaceutically acceptable excipient, e.g., carrier. In some embodiments, the compositions of the disclosure are formulated for the prevention, treatment, or management of a health condition such as cancer, an immune disease, or chronic infection. For example, the compositions of the disclosure can be formulated as a prophylactic composition, a therapeutic composition, or a pharmaceutical composition comprising a pharmaceutically acceptable excipient, or a mixture thereof. In some embodiments, the compositions of the present disclosure are formulated for use as a biotherapeutic. In some embodiments, the compositions of the present application are formulated for use as an adjuvant.

Accordingly, in one aspect, provided herein are pharmaceutical compositions including a pharmaceutically acceptable excipient and: a) a nucleic acid construct of the disclosure; b) a recombinant cell of the disclosure; and/or c) a recombinant polypeptide of the disclosure.

Non-limiting exemplary embodiments of the pharmaceutical compositions of the disclosure can include one or more of the following features. The nucleic acid constructs of the disclosure can be used in a naked form or formulated with a delivery vehicle. Exemplary routes, either using in a free form, e.g., inserted into a nucleic acid, e.g., a vector. For example, as described in greater detail below, a nucleic acid construct as described herein can be used as a vaccine.

For use in a pharmaceutical composition of the disclosure, a nucleic acid, or a recombinant cell as described herein can be formulated into or with delivery vehicles. Exemplary delivery vehicles suitable for the compositions and methods of the disclosure include, but are not limited to liposomes (e.g., neutral or anionic liposomes), microspheres, immune stimulating complexes (ISCOMS), lipid-based nanoparticles (LNP), polymer nanoparticles, viral replicon particles (VRPs), or conjugated with bioactive ligands, which can facilitate delivery and/or enhance the immune response. These compounds are readily available to one skilled in the art; for example, see Liposomes: A Practical Approach, RCP New Ed, IRL press (1990). Adjuvants other than liposomes and the like are also used and are known in the art. Adjuvants may protect the antigen (e.g., srRNA construct) from rapid dispersal by sequestering it in a local deposit, or they may contain substances that stimulate the host to secrete factors that are chemotactic for macrophages and other components of the immune system. An appropriate selection can be made by those skilled in the art, for example, from those described below.

Accordingly, in some embodiments, a composition of the disclosure can include one or more of the following: physiologic buffer, a liposome, a lipid-based nanoparticle (LNP), a polymer nanoparticle, a viral replicon particle (VRP), a microsphere, an immune stimulating complex (ISCOM), a conjugate of bioactive ligand, or a combination of any thereof.

In some embodiments, the nucleic acid constructs of the disclosure can be delivered to a cell or a subject by a lipid-based nanoparticle (LNP). LNP are generally less immunogenic than viral particles. While many humans have preexisting immunity to viral particles there is no pre-existing immunity to LNP. In addition, adaptive immune response against LNP is unlikely to occur which enables repeat dosing of LNP.

The lipids suitable for the compositions and methods described herein can be cationic lipids, ionizable cationic lipids, anionic lipids, or neutral lipids.

In some embodiments, the LNP of the disclosure can include one or more ionizable lipids. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes lipids that assume a positive charge on pH decrease from physiological pH, and any of a number of lipid species that carry a net positive charge at a selective pH, such as physiological pH. Permanently cationic lipids such as DOTMA have proven too toxic for clinical use. The ionizable lipid can be present in lipid formulations according to other embodiments, preferably in a ratio of about 30 to about 70 Mol %, in some embodiments, about 30 Mol %, in other embodiments, about 40 Mol %, in other embodiments, about 45 Mol % in other embodiments, about 47.5 Mol % in other embodiments, about 50 Mol %, in still other embodiments, and about 60 Mol % in yet others ("Mol %" means the percentage of the total moles that is of a particular component). The term "about" in this paragraph signifies a plus or minus range of 5 Mol %. DODMA, or 1,2-dioleyloxy-3-dimethylaminopropane, is an ionizable lipid, as is DLin-MC3-DMA or 0-(Z,Z,Z,Z-heptatriaconta-6,9,26,29-tetraen-19-yl)-4-(N,N-dimethylamino) ("MC3").

Exemplary ionizable lipids suitable for the compositions and methods of the disclosure includes those described in PCT publications WO2020252589A1 and WO2021000041A1, U.S. Pat. Nos. 8,450,298 and 10,844,028, and Love K. T. et al., *Proc Natl Acad Sci USA*, Feb. 2, 2010 107 (5) 1864-1869, all of which are hereby incorporated by reference in their entirety. Accordingly, in some embodiments, the LNP of the disclosure includes one or more lipid compounds described in Love K. T. et al., 2010 supra, such as C16-96, C14-110, and C12-200. In some embodiments, the LNP includes an ionizable cationic lipid selected from the group consisting of ALC-0315, C12-200, LN16, MC3, MD1, SM-102, and a combination of any thereof. In some embodiments, the LNP of the disclosure includes C12-200. The structure of C12-200 lipid is known in the art and described in, e.g., U.S. Pat. Nos. 8,450,298 and 10,844,028, which are hereby incorporated by reference in their entirety. In some embodiments the C12-200 is combined with cholesterol, C14-PEG2000, and DOPE. In some embodiments, the C12-200 is combined with DSPC and DMG-PEG2000.

In some embodiments, the LNP of the disclosure includes one or more cationic lipids. Suitable cationic lipids include, but are not limited to, 98N12-5, C12-200, C14-PEG2000, DLin-KC2-DMA (KC2), DLin-MC3-DMA (MC3), XTC, MD1, and 7C1. In some embodiments, the LNP of the disclosure includes one or more neutral lipids. Non-limiting neutral lipids suitable for the compositions and methods of the disclosure include DPSC, DPPC, POPC, DOPE, and SM. In some embodiments, the LNP of the disclosure includes one or more ionizable lipid compounds described in PCT publications WO2020252589A1 and WO2021000041A1, which are hereby incorporated by reference in their entirety.

A number of other lipids or combination of lipids that are known in the art can be used to produce a LNP. Non-limiting examples of lipids suitable for use to produce LNPs include DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Non-limiting examples of cationic lipids include 98N12-5, C12-200, C14-PEG2000, DLin-KC2-DMA (KC2), DLin-MC3-DMA (MC3), XTC, MD1, 7C1, and a combination of any thereof. Non-limiting examples of neutral lipids include DPSC, DPPC, POPC, DOPE, and SM. Non-limiting examples of PEG-modified lipids include PEG-DMG, PEG-CerC14, and PEG-CerC20.

In some embodiments, the LNP of the disclosure includes at least one lipid selected from the group consisting of C12-200, C14-PEG2000, DOPE, DMG-PEG2000, DSPC, DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). In some embodiments the C12-200 is combined with cholesterol, C14-PEG2000, and DOPE. In some embodiments, the C12-200 is combined with DSPC and DMG-PEG2000.

In some embodiments, the mass ratio of lipid to nucleic acid in the LNP delivery system is about 100:1 to about 3:1, about 70:1 to 10:1, or 16:1 to 4:1. In some embodiments, the mass ratio of lipid to nucleic acid in the LNP delivery system is about 16:1 to 4:1. In some embodiments, the mass ratio of lipid to nucleic acid in the LNP delivery system is about 20:1. In some embodiments, the mass ratio of lipid to nucleic acid in the LNP delivery system is about 8:1. In some embodiments, the lipid-based nanoparticles have an average diameter of less than about 1000 nm, about 500 nm, about 250 nm, about 200 nm, about 150 nm, about 100 nm, about 75 nm, about 50 nm, or about 25 nm. In some embodiments, the LNPs have an average diameter ranging from about 70 nm to 100 nm. In some embodiments, the LNPs have an average diameter ranging from about 88 nm to about 92 nm, from 82 nm to about 86 nm, or from about 80 nm to about 95 nm.

In some embodiments, the compositions of the disclosure that formulated in a liposome. In some embodiments, the compositions of the disclosure that formulated in a lipid-based nanoparticle (LNP). In some embodiments, the compositions of the disclosure that formulated in a polymer nanoparticle.

As described above, neural lipids, also known as "structural lipids" or "helper lipids" can also be incorporated into lipid formulations and lipid particles in some embodiments. The lipid formulations and lipid particles can include one or more structural lipids at about 10 to 40 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, di stearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (trans DOPE).

In another embodiment, the structural lipid can be any lipid that is negatively charged at physiological pH. These lipids include phosphatidylglycerols such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizing agents can be included in lipid formulations embodiments to ensure integrity of the mixtures. Stabilizing agents are a class of molecules which disrupt or help form the hydrophobic-hydrophilic interactions among molecules. Suitable Stabilizing agents include, but are not limited to, polysorbate 80 (also known as Tween 80, 1UPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate), and Brij™ S10 (Polyoxyethylene (10) stearyl ether). Polyethylene glycol conjugated lipids may also be used. The stabilizing agents may be used alone or in combinations with each other.

In some embodiments, the stabilizing agents comprises about 0.1 to 3 Mol % of the overall lipid mixture. In some embodiments, the stabilizing agents comprise about 0.5 to 2.5 Mol % of the overall lipid mixture. In some embodiments, the stabilizing agent is present at greater than 2.5 Mol %. In some embodiments the stabilizing agent is present at 5 Mol %. In some embodiments the stabilizing agent is present at 10 Mol %. In some embodiments, the stabilizing agent is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth. In other embodiments, the stabilizing agent is 2.6-10 Mol % of the lipid mixture. In other embodiments, the stabilizing agents is present at greater than 10 Mol % of the lipid mixture.

Steroids can also be included in the lipid compositions for certain applications, and lipid particles made therefrom include sterols, such as cholesterol and phytosterol.

In some embodiments, the therapeutic compositions described herein, e.g., nucleic acid constructs, recombinant cells, recombinant polypeptides, and/or pharmaceutical compositions are incorporated into therapeutic compositions for use in methods of preventing or treating a subject who has, who is suspected of having, or who may be at high risk for developing a cancer.

In some embodiments, the compositions are immunogenic compositions, e.g., composition that can stimulate an immune response in a subject. In some embodiments, the immunogenic compositions are formulated as a vaccine. In some embodiments, the pharmaceutical compositions are formulated as an adjuvant. In some embodiments, the immunogenic compositions are formulated as a biotherapeutic, e.g., vehicle for gene delivery of different molecules with bioactivity. Non-limiting examples of biotherapeutic include cytokines, chemokines, and other soluble immunomodulators, enzymes, peptide and protein agonists, peptide and protein antagonists, hormones, receptors, antibodies and antibody-derivatives, growth factors, transcription factors, and gene silencing/editing molecules. In some embodiments, the pharmaceutical compositions are formulated as an adjuvant.

In some embodiments, the immunogenic compositions are substantially non-immunogenic or minimally immunogenic (e.g. compositions that minimally stimulate an immune response in a subject. In some embodiments, the non-immunogenic or minimally immunogenic compositions are formulated as a biotherapeutic. In some embodiments, the pharmaceutical compositions are formulated for one or more of intranasal administration, transdermal administration, intraperitoneal administration, intramuscular administration, intranodal administration, intratumoral administration, intraarticular administration, intravenous administration, subcutaneous administration, intravaginal administration, and oral administration.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS), tris (tromethamine), and HEPES. In these cases, the composition should be sterile and should be fluid to the extent that easy syringability exists. It can be stable under the conditions of manufacture and storage, and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, sucrose, trehalose, and/or sodium chloride in the composition. In some embodiments, the composition comprises tris and sucrose. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the composition is formulated for one or more of intranasal administration, transdermal administration, intramuscular administration, intratumoral administration, intranodal administration, intravenous administration, intraperitoneal administration, oral administration, intravaginal, or intra-cranial administration.

Methods of the Disclosure

Administration of any one of the therapeutic compositions described herein, e.g., nucleic acid constructs, recombinant cells, recombinant polypeptides, and/or pharmaceutical compositions, can be used for inducing at least one pharmacodynamics effect in a subject. In some embodiments, the nucleic acid constructs, recombinant cells, recombinant polypeptides, and/or pharmaceutical compositions as described herein can result in induced production of one or more of the following: immune responses and mediators such as interferon gamma (IFNγ). In some embodiments, the administered compositions described herein enhance tumor immunity in a tumor microenvironment. In some embodiments, the subject has, is suspected of having, or may be at high risk for developing one or more relevant health conditions or diseases. In some embodiments, the subject has a cancer, an immune disease, or a chronic infection. In some embodiments, the subject is a patient under the care of a physician.

Examples of immune diseases suitable for the methods of the disclosure include, but are not limited to, rheumatoid arthritis, osteoarthritis, Still's disease, Familiar Mediterranean Fever, systemic sclerosis, multiple sclerosis, ankylosing spondylitis, Hashimoto's tyroidism, systemic lupus erythematosus, Sjogren's syndrome, diabetic retinopathy, diabetic vasculopathy, diabetic neuralgia, insulitis, psoriasis, alopecia greata, warm and cold autoimmune hemolytic anemia (AIHA), pernicious anemia, acute inflammatory diseases, autoimmune adrenalitis, chronic inflammatory demyelinating polyneuropathy (CIDP), Lambert-Eaton syndrome, lichen sclerosis, Lyme disease, Graves disease, Behçet's disease, Ménière's disease, reactive arthritis (Reiter's syndrome), Churg-Strauss syndrome, Cogan syndrome, CREST syndrome, pemphigus vulgaris and pemphigus *foliaceus*, bullous pemphigoid, polymyalgia rheumatica, polymyositis, primary biliary cirrhosis, pancreatitis, peritonitis, psoriatic arthritis, rheumatic fever, sarcoidosis, Sjörgensen syndrome, scleroderma, celiac disease, stiff-man syndrome, Takayasu arteritis, transient gluten intolerance, autoimmune uveitis, vitiligo, polychondritis, dermatitis herpetiformis (DH) or Duhring's disease, fibromyalgia, Goodpasture syndrome, Guillain-Barré syndrome, Hashimoto thyroiditis, autoimmune hepatitis, inflammatory bowel disease (IBD), Crohn's disease, colitis ulcerosa, myasthenia gravis, immune complex disorders, glomerulonephritis, polyarteritis nodosa, anti-phospholipid syndrome, polyglandular autoimmune syndrome, idiopathic pulmonar fibrosis, idiopathic thrombocytopenic purpura (ITP), urticaria, autoimmune infertility, juvenile rheumatoid arthritis, sarcoidosis, and autoimmune cardiomyopathy.

Non-limiting examples of infection suitable for the methods of the disclosure include infections with viruses such as human immunodeficiency virus (HIV), hepatitis B virus (HBV), hepatitis B virus (HCV), Cytomegalovirus (CMV), respiratory syncytial virus (RSV), human papillomavirus (HPV), Epstein-Barr virus (EBV), severe acute respiratory syndrome coronavirus 2 (SARS-CoV2), severe acute respiratory syndrome coronavirus (SARS-CoV), Middle East Respiratory Syndrome (MERS), influenza virus, and Ebola virus. Additional infections suitable for the methods of the disclosure include infections with intracellular parasites such as *Leishmania, Rickettsia, Chlamydia, Coxiella, Plasmodium, Brucella*, mycobacteria, *Listeria, Toxoplasma* and *Trypanosoma*.

In some embodiments, the nucleic acid constructs, recombinant cells, recombinant RNA molecules, recombinant polypeptides, and/or pharmaceutical compositions, can be useful in the treatment and/or prevention of immune diseases, autoimmune diseases, or inflammatory diseases such as, for example, glomerulonephritis, inflammatory bowel disease, nephritis, peritonitis, psoriatic arthritis, osteoarthritis, Still's disease, Familiar Mediterranean Fever, systemic scleroderma and sclerosis, inflammatory bowel disease (IBD), Crohn's disease, ulcerative colitis, acute lung injury, meningitis, encephalitis, uveitis, multiple myeloma, glomerulonephritis, nephritis, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, hemolytic anemia, myasthenia gravis, lupus nephritis, lupus erythematosus, rheumatoid arthritis (RA), ankylosing spondylitis, pemphigus, Graves' disease, Hashimoto's thyroiditis, small vessel vasculitides, Omen's syndrome, chronic renal failure, autoimmune thyroid disease, acute infectious mononucleosis, HIV, herpes virus associated diseases, human virus infections, coronavirus, other enterovirus, herpes virus, influenza virus, parainfluenza virus, respiratory syncytial virus or adenovirus infection, bacteria pneumonia, wounds, sepsis, cerebral stroke/cerebral edema, ischaemia-reperfusion injury, and hepatitis C Non-limiting examples of inflammatory suitable for the methods of the disclosure include inflammatory diseases such as asthma, inflammatory bowel disease (IBD), chronic colitis, splenomegaly, and rheumatoid arthritis. In one aspect, provided herein are methods for inducing a pharmacodynamic effect in a subject, the methods include administering to the subject a composition including one or more of the following: (a) a nucleic acid construct as described herein; (b) a recombinant cell as described herein; and (b) a pharmaceutical composition as described herein. In some embodiments, the pharmacodynamic effect includes eliciting an immune response in the subject.

Non-limiting exemplary embodiments of the methods for inducing a pharmacodynamic effect can include one or more of the following features. In some embodiments, the administered composition induces production of one or more pro-inflammatory molecules in the subject. In some embodiments, the one or more pro-inflammatory molecules includes interferon gamma (IFNγ), cytokines, TNF-α, GM-CSF, and MIP1α, granzyme B, granzyme A, perforin, or a combination of any thereof. In some embodiments, the administered compositions inhibits production of one or both of IL-1α or IL-1β signaling pathways. In some embodiments, the administered compositions induces perturbation of IL-6 or VEGF expression levels, angiogenesis, tumor metastasis, immune suppression, or tissue remodeling. In some embodiments, the subject has been previously treated with one or more therapies and has developed at least a partial resistance to said one or more therapies. In some embodiments, at least one of the one or more therapies includes a small molecule. In some embodiments, the subject has a cancer, an immune disease, or a chronic infection.

As described above, administration of any one of the therapeutic compositions described herein, e.g., nucleic acid constructs, recombinant cells, recombinant polypeptides, and/or pharmaceutical compositions, can be used for inducing at least one pharmacodynamic effect in a subject. In some embodiments, the analysis of the nucleic acid constructs, recombinant cells, recombinant polypeptides, and/or pharmaceutical compositions described herein for their capacity to confer at least one pharmacodynamic effect is carried out in vivo or ex vivo. Examples of pharmacodynamic effects that can be analyzed include: immunogenicity effect (e.g., eliciting an immune response in vivo), a biomarker response, a therapeutic effect, a prophylactic effect, a desired effect, an undesired effect, an adverse effect, and effect in a disease model. In some embodiments, the assessment of pharmacodynamic effects includes assessing induction of an immune response in vivo. In some embodiments, the assessment of pharmacodynamic effects includes assessing induction of cytokine pathways that can potentiate an immune response and prevent angiogenesis and metastasis In some embodiments, the disclosed composition is formulated to be compatible with its intended route of administration. For example, the nucleic acid constructs, recombinant cells, recombinant polypeptides, and/or pharmaceutical compositions of the disclosure may be given orally, by inhalation, or through a parenteral route. Examples of parenteral routes of administration include, for example, intramuscular, intratumoral, intraocular, intravenous, intranodal, intradermal, subcutaneous, transdermal (topical), transmucosal, intravaginal, and rectal administration. In some embodiments, the composition is administered intramuscularly. In some embodiments, the composition is administered intratumorally. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates, phosphates, tris, sucrose and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

The therapeutic compositions described herein, e.g., nucleic acid constructs, recombinant cells, recombinant polypeptides, and/or pharmaceutical compositions, can be administered one from one or more times per day to one or more times per week; including once every other day. Treatment of a subject with a therapeutically effective amount of the subject nucleic acid constructs, recombinant cells, recombinant polypeptides, and/or pharmaceutical compositions of the disclosure can include a single treatment or, can include a series of treatments. In some embodiments, the compositions are administered at weekly intervals, e.g., 1 to 2, 2 to 3, or 3 to 4 doses given at 1 to 2, 2 to 3, or 3 to 4 week intervals. This may be followed with an additional administration every 1, 2, 3, or 4 months. In some embodiments, 3 doses can be administered intramuscularly at a 3 to 4 week interval, followed by intramuscular administration every 3 months. Alternatively, the composition can be administered at shorter intervals, e.g., every 8 hours for five days, followed by a rest period of 2 to 14 days, e.g., 9 days, followed by an additional five days of administration every 8 hours. With regard to nucleic acid constructs and recombinant polypeptides, the therapeutically effective amount of a nucleic acid construct or recombinant polypeptide of the disclosure (e.g., an effective dosage) depends on the nucleic acid construct or recombinant polypeptide selected.

As discussed supra, a therapeutically effective amount includes an amount of a therapeutic composition that is sufficient to promote a particular effect when administered to a subject, such as one who has, is suspected of having, or is at risk for a health condition, e.g., a cancer. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease.

A treatment is considered effective treatment if at least any one or all of the signs or symptoms of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in a subject or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

In some embodiments, the nucleic acid constructs, recombinant cells, recombinant polypeptides, and/or pharmaceutical compositions of the disclosure can be administered to a subject in a composition having a pharmaceutically acceptable carrier and in an amount effective to stimulate an immune response. Generally, a subject can be immunized through an initial series of injections (or administration through one of the other routes described below) and subsequently given boosters to increase the protection afforded by the original series of administrations. The initial series of injections and the subsequent boosters are administered in such doses and over such a period of time as is necessary to stimulate an immune response in a subject. In some embodiments of the disclosed methods, the subject is a mammal. In some embodiments, the mammal is a human subject.

As described above, pharmaceutically acceptable carriers suitable for injectable use include sterile aqueous solutions (where water soluble) or dispersions and sterile powders for the extemporaneous preparation of sterile injectable solutions or dispersions. In these cases, the composition must be sterile and must be fluid to the extent that easy syringability exists. The composition must further be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, etc.), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like.

Sterile injectable solutions can be prepared by incorporating the nucleic acid constructs, recombinant cells, and/or recombinant polypeptides in the required mount in an appropriate solvent with one or a combination of ingredients enumerated above, as required, followed by filtered sterilization.

When the nucleic acid constructs, recombinant cells, recombinant polypeptides, and/or pharmaceutical compositions are suitably protected, as described above, they may be orally administered, for example, with an inert diluent or an assimilable edible carrier. The nucleic acid constructs, recombinant cells, recombinant polypeptides, and/or pharmaceutical compositions and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like.

Additional Therapies

In some embodiments, a composition according to the present disclosure is administered to the subject individually as a single therapy (monotherapy) or as a first therapy in combination with at least one additional therapies (e.g., second therapy). In some embodiments, the second therapy is selected from the group consisting of chemotherapy, radiotherapy, immunotherapy, hormonal therapy, toxin therapy, targeted therapy, and surgery. In some embodiments, the second therapy is selected from the group consisting of chemotherapy, radiotherapy, immunotherapy, hormonal therapy, toxin therapy or surgery. In some embodiments, the first therapy and the second therapy are administered concomitantly. In some embodiments, the first therapy is administered at the same time as the second therapy. In some embodiments, the first therapy and the second therapy are administered sequentially. In some embodiments, the first therapy is administered before the second therapy. In some embodiments, the first therapy is administered after the second therapy. In some embodiments, the first therapy is administered before and/or after the second therapy. In some embodiments, the first therapy and the second therapy are administered in rotation. In some embodiments, the first therapy and the second therapy are administered together in a single formulation.

Kits

Also provided herein are various kits for the practice of a method described herein as well as written instructions for making and using the same. In particular, some embodiments of the disclosure provide kits for inducing a pharmacodynamics effect in a subject. Some other embodiments relate to kits for methods of treating cancer in a subject in need thereof. For example, provided herein, in some embodiments, are kits that include one or more of the nucleic acid constructs, recombinant cells, recombinant polypeptides, and/or pharmaceutical compositions as provided and described herein, as well as written instructions for making and using the same.

In some embodiments, the kits of the disclosure further include one or more means useful for the administration of any one of the provided nucleic acid constructs, recombinant cells, recombinant polypeptides, and/or pharmaceutical compositions to a subject. For example, in some embodiments, the kits of the disclosure further include one or more syringes (including pre-filled syringes) and/or catheters (including pre-filled syringes) used to administer any one of the provided nucleic acid constructs, recombinant cells, recombinant polypeptides, and/or pharmaceutical compositions to a subject. In some embodiments, a kit can have one or more additional therapeutic agents that can be administered simultaneously or sequentially with the other kit components for a desired purpose, e.g., for diagnosing, preventing, or treating a condition in a subject in need thereof.

Any of the above-described kits can further include one or more additional reagents, where such additional reagents can be selected from: dilution buffers; reconstitution solutions, wash buffers, control reagents, control expression vectors, negative controls, positive controls, reagents suitable for in vitro production of the provided nucleic acid constructs, recombinant cells, recombinant polypeptides, and/or pharmaceutical compositions of the disclosure.

In some embodiments, the components of a kit can be in separate containers. In some other embodiments, the components of a kit can be combined in a single container. Accordingly, in some embodiments of the disclosure, the kit includes one or more of the nucleic acid constructs, recombinant cells, recombinant polypeptides, and/or pharmaceutical compositions as provided and described herein in one container (e.g., in a sterile glass or plastic vial) and a further therapeutic agent in another container (e.g., in a sterile glass or plastic vial).

In another embodiment, the kit includes a combination of the compositions described herein, including one or more nucleic acid constructs, recombinant cells, and/or recombinant polypeptides of the disclosure in combination with one or more further therapeutic agents formulated together, optionally, in a pharmaceutical composition, in a single, common container.

If the kit includes a pharmaceutical composition for parenteral administration to a subject, the kit can include a device (e.g., an injection device or catheter) for performing such administration. For example, the kit can include one or more hypodermic needles or other injection devices as discussed above containing one or more nucleic acid constructs, recombinant cells, and/or recombinant polypeptides of the disclosure.

In some embodiments, a kit can further include instructions for using the components of the kit to practice the methods disclosed herein. For example, the kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the disclosure may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and intellectual property information.

The instructions for practicing the methods are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the Applicant reserves the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

Additional embodiments are disclosed in further detail in the following examples, which are provided by way of illustration and are not in any way intended to limit the scope of this disclosure or the claims.

EXAMPLES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B. V., the disclosures of which are incorporated herein by reference.

Additional embodiments are disclosed in further detail in the following examples, which are provided by way of illustration and are not in any way intended to limit the scope of this disclosure or the claims.

Example 1

Construction of Alphavirus Vectors

This Example describes the experiments performed to construct base alphavirus vectors (e.g., without a heterologous gene) that were subsequently used for construction of vectors that express a gene or genes of interest (e.g., IL-12 p35 subunit or functional variants thereof, IL-12 p40 subunit or functional variants thereof, and IL-1RA or functional variant thereof).

EEEV Base Vector

The base EEEV vector (i.e. without a heterologous gene of interest) was constructed as follows: The base EEEV vector was synthesized de novo in four ~4 kb parts (Twist Bioscience) from a reference sequence (Genbank EF151502) with several modifications. Silent mutations G301A, A3550C, G4516A, G5725A, G7399A mutations were incorporated to eliminate restriction enzyme cut sites. A unique restriction enzyme cut site (SpeI, 5'-A'CTAG,T-3') was incorporated in place of the coding sequence of the native EEEV structural genes (where the 5' A matches the location of the structural polyprotein ATG start codon, and the 3' T matches the location of the structural polyprotein stop codon TAA). A 5' adaptor sequence (5'-CTGGAGACGTGGAGGAGAACCCTGGACCT-3'; SEQ ID NO: 11) was inserted upstream of the SpeI site, and a 3' adaptor sequence (5'-GACCGCTACGCCCCAATGACCCGACCAGC-3'; SEQ ID NO: 12) was inserted downstream of the SpeI site for subsequent Gibson Assembly® procedures (Gibson et al., *Nat. Methods* 6, 343-345, 2009). A bacteriophage T7 RNA polymerase promoter (5'-TAATACGACTCACTATAG-3'; SEQ ID NO: 13) was included upstream of the EEEV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 14) followed by a unique restriction enzyme cut site (NotI, 5'-GC'GGCC,GC-3'). The parts were combined in a five-piece Gibson Assembly® reaction: a linearized pYL backbone and the four synthesized fragments to result in the EEEV base vector.

CHIKV Base Vectors

The base CHIKV S27 vector was synthesized de novo in four ~4 kb parts (Twist Bioscience, Thermo Fisher GeneArt) from a reference sequence (Genbank AF369024) with a silent A5366G mutation, and with a unique restriction enzyme cut site (SpeI, 5'-A'CTAG,T-3') in place of the coding sequence of the CHIKV structural genes (where the 5' A matches the location of the structural polyprotein's ATG start codon, and the 3' T matches the location of the structural polyprotein's stop codon TAA). A 5' adaptor sequence (5'-CTGGAGACGTGGAGGAGAACCCTGGACCT-3'; SEQ ID NO: 11) was inserted upstream of the SpeI site, and a 3' adaptor sequence (5'-GACCGCTACGCCCCAATGACCCGACCAGC-3'; SEQ ID NO: 12) was inserted downstream of the SpeI site for subsequent Gibson Assembly® procedures. A bacteriophage T7 RNA polymerase promoter (5'-TAATACGACTCACTATAG-3'; SEQ ID NO: 13) was included upstream of the CHIKV genome sequence, and downstream contained a poly(A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 14) followed by a unique restriction enzyme cut site (NotI, 5'-GC'GGCC,GC-3'). The parts were combined in a five-piece Gibson Assembly® reaction a linearized pYL backbone and the four synthesized fragments to result in the CHIKV S27 base vector.

The CHIKV DRDE base vector was similarly constructed from a reference sequence (Genbank EF210157), except the S27 3' UTR was used in place of the DRDE 3' UTR.

SINV Base Vectors

The base SINV Girdwood vector was synthesized de novo in four ~4 kb parts (Twist Bioscience, Thermo Fisher GeneArt) from a Girdwood strain reference sequence (Genbank MF459683) with a unique restriction enzyme cut site (SpeI, 5'-A'CTAG,T-3') in place of the coding sequence of the SINV structural genes (where the 5' A is the next nucleotide after a P2A sequence following nucleotide 93 of the structural polyprotein gene, and the 3' T matches the location of the structural polyprotein's stop codon TGA). A bacteriophage T7 RNA polymerase promoter (5'-TAATACGACTCACTATAG-3'; SEQ ID NO: 13) was included upstream of the SINV genome sequence, and downstream contained a poly(A) sequence followed by a SapI site, which cuts upstream of the recognition site. Immediately downstream of the SapI site is a T7 terminator sequence (5'-AACCCCTCTCTAAACG-GAGGGGTTTTTTT-3'; SEQ ID NO: 14) followed by a unique restriction enzyme cut site (NotI, 5'-GC'GGCC,GC-3'). The parts were combined in a five-piece Gibson Assembly® reaction (e.g., a linearized pYL backbone and the four synthesized fragments) to result in the SINV Girdwood base vector.

The base SINV AR86 vector was similarly constructed from a reference sequence (Genbank U38305), except the nsP2 coding sequence was derived from the Girdwood reference sequence.

VEE Base Vector

The base VEE vector was synthesized de novo in four ~4 kb parts (Twist Bioscience, Thermo Fisher GeneArt) from a TC-83 strain reference sequence (Genbank L01443) with a silent A2087G mutation, and a unique restriction enzyme cut site (SpeI, 5'-A'CTAG,T-3') in place of the coding sequence of the VEE structural genes (where the 5' A is the next nucleotide after a P2A sequence following nucleotide 93 of the structural polyprotein gene, and the 3' T matches the location of the structural polyprotein's stop codon TGA). A 5' adaptor sequence (5'-CTGGAGACGTGGAG-GAGAACCCTGGACCT-3'; SEQ ID NO: 11) was inserted upstream of the SpeI site, and a 3' adaptor sequence (5'-GACCGCTACGCCCCAATGACCCGACCAGC-3'; SEQ ID NO: 12) was inserted downstream of the SpeI site for subsequent Gibson Assembly® procedures. A bacteriophage T7 RNA polymerase promoter (5'-TAATACGACTCAC-TATAG-3'; SEQ ID NO: 13) was included upstream of the VEE genome sequence, and downstream contained a poly (A) sequence followed by a SapI site, which cuts upstream of the recognition site. Immediately downstream of the SapI site is a T7 terminator sequence (5'-AACCCCTCTCTAAACGGAGGGGTTTTTTT-3'; SEQ ID NO: 14) followed by a unique restriction enzyme cut site (NotI, 5'-GC'GGCC,GC-3'). The parts were combined in a five-piece Gibson Assembly® reaction (e.g., a linearized pYL backbone and the four synthesized fragments) to result in the VEE base vector.

Final Vectors

Construction of a vectors containing heterologous genes was carried out as follows: the empty base vector was linearized by SpeI digestion. The IL-12A, IL12-B, IL-1RN genes were codon optimized/refactored for human expression in silico and along with the EMCV IRES were synthesized de novo (IDT). The synthetic products were amplified using primers which added either 5' and 3' adaptor sequences to the ends of the genes, or primers which added P2A sequences and/or sequences of homology to neighboring gene inserts. The digestion product and PCR products were combined by Gibson Assembly® procedure to result in the final vectors.

Example 2

In Vitro Evaluation of Modified Alphavirus Vectors

This Example describes the results of in vitro experiments performed to evaluate expression levels of the synthetic srRNA constructs described in Example 1 above, and to investigate any differential behavior thereof (e.g., replication and protein expression).

In vitro transcription: RNA was prepared by in vitro transcription from a SapI-linearized plasmid template with bacteriophage T7 polymerase with either a 5' ARCA cap (HiScribe™ T7 ARCA mRNA Kit, NEB) or by uncapped transcription (HiScribe™ T7 High Yield RNA Synthesis Kit, NEB) followed by addition of a 5' cap 1 (Vaccinia Capping System, mRNA Cap 2'-O-Methyltransferase, NEB). RNA was then purified using phenol/chloroform extraction, or column purification (Monarch® RNA Cleanup Kit, NEB). RNA concentration was determined by absorbance at 260 nm (Nanodrop, Thermo Fisher Scientific).

Replication: RNA was transformed by electroporation into BHK-21 or Vero cells (e.g., 4D-Nucleofector™, Lonza). At 15-22 hours following transformation, the cells were fixed and permeabilized (eBioscience™ Foxp3/Transcription Factor Staining Buffer Set, Invitrogen) and stained using a PE-conjugated anti-dsRNA mouse monoclonal antibody (J2, Scicons) to quantify the frequency of dsRNA+ cells and the mean fluorescence intensity (MFI) of dsRNA in individual cells by fluorescence flow cytometry.

Protein expression by ELISA: Human IL-12p'70 and IL-1RA were detected from electroporated BHK-21 cells with 500 ng of srRNA monogenic or multigenic constructs. Supernatants were harvested at approximately 24 and 48 hours after transfection and assayed with Human IL-12p70 from RnD Systems (cat #DY1270) and Human IL-1ra/IL-1F3 DuoSet ELISA from RnD Systems (cat #DY280).

Bioactivity assay: Human IL-12p70 and IL-1RA were detected from electroporated BHK-21 cells with 500 ng of srRNA monogenic or multigenic constructs. Supernatants were harvested at approximately 24 and 48 hours after transfection and assayed with GloMax bioassay from Promega for IL-12 (cat #JA2601). IL-1RA was assayed using IL-1β Reporter HEK 293 Cells (Invivogen, hkb-il1bv2) in the pre-incubated with 4 ng/mL IL1β (1 ng/mL final) and supernatants from transfected BHK cells as per the manufacturer's protocol.

Evaluation of Number and Ordinality of Genes

Figure 3:
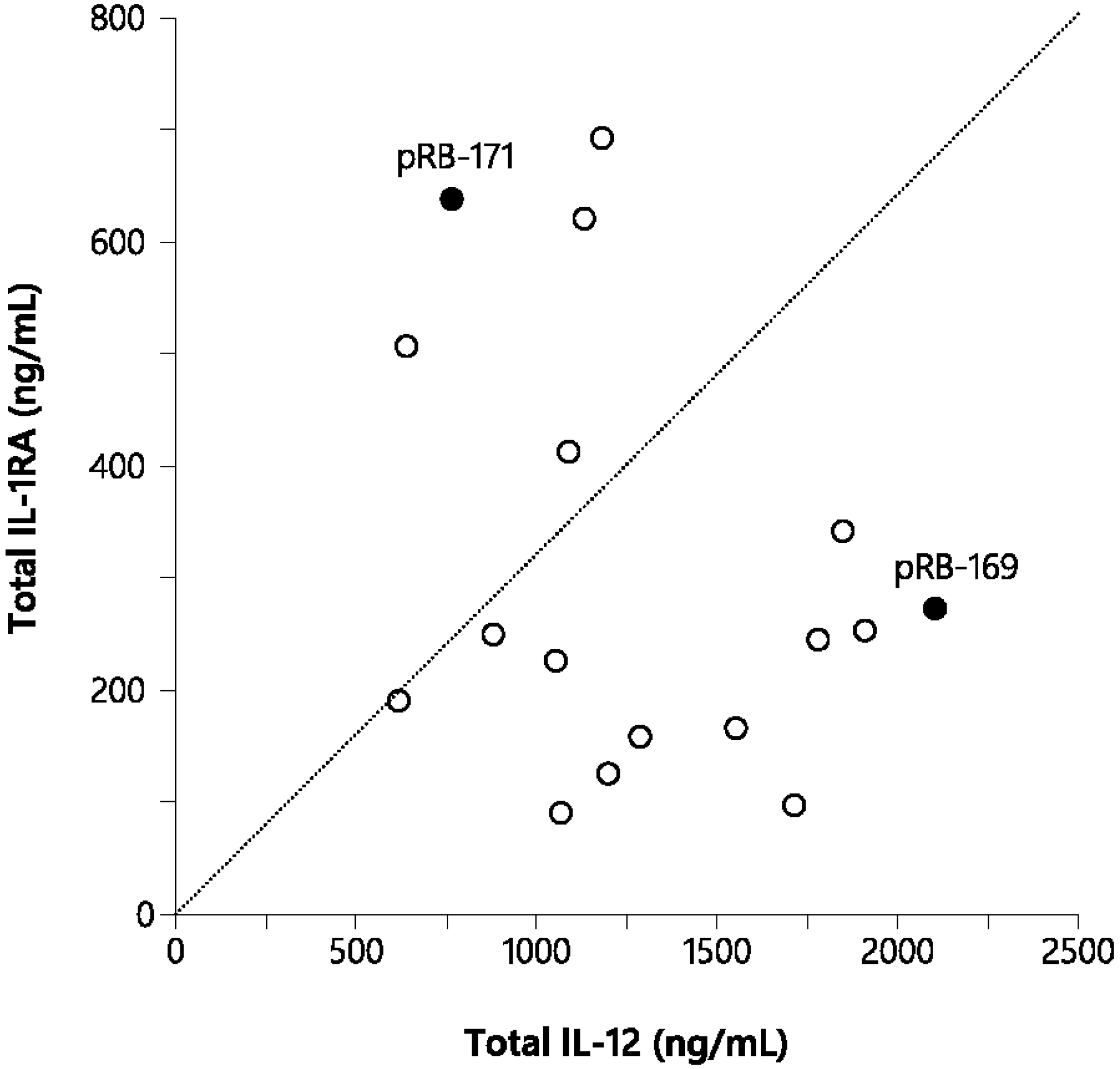
FIG. 3 is a graphical representation of combined IL-12 bioactivity and IL-1RA expression data from srRNA constructs.
Figure 4A:
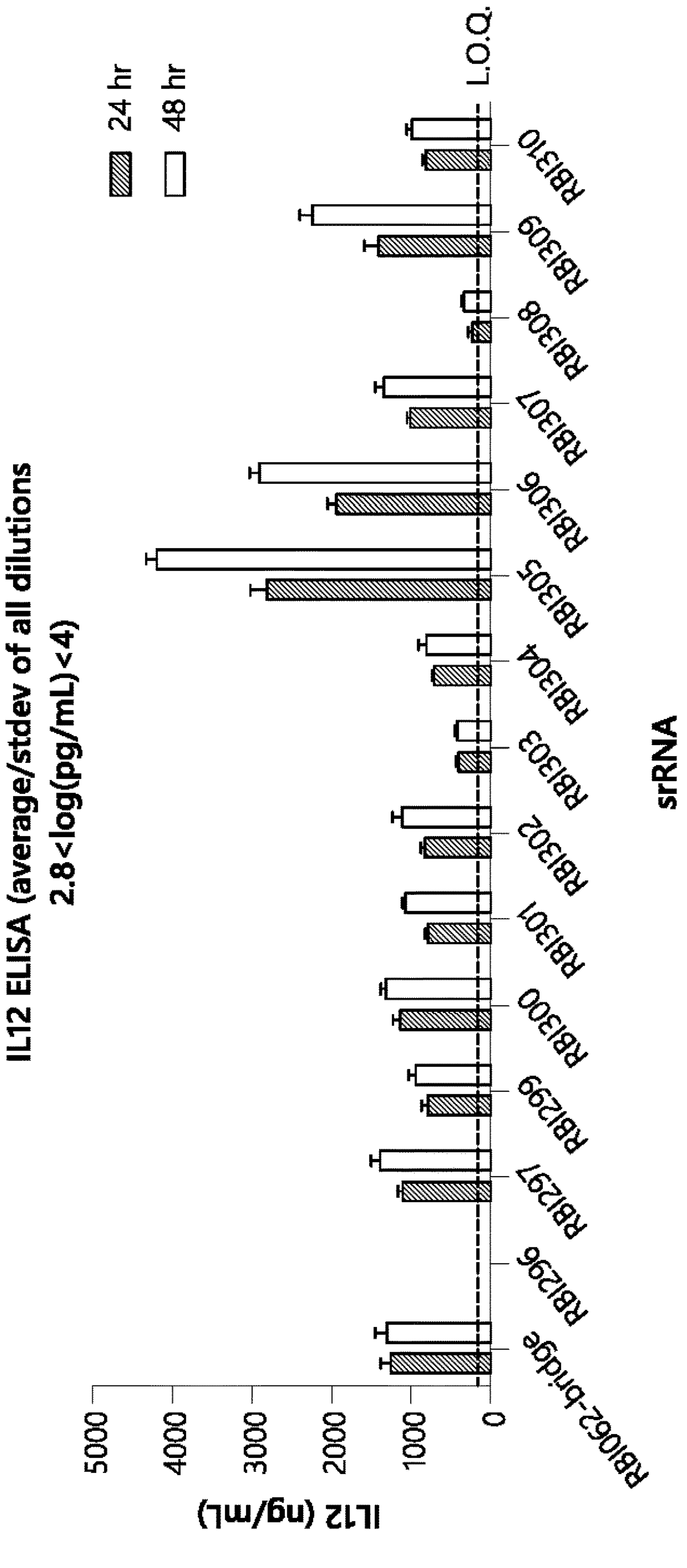
FIGS. 4A-4B are graphical representations of protein expression from the two best multigenic configurations cloned into six different srRNA vectors.
Figure 4B:
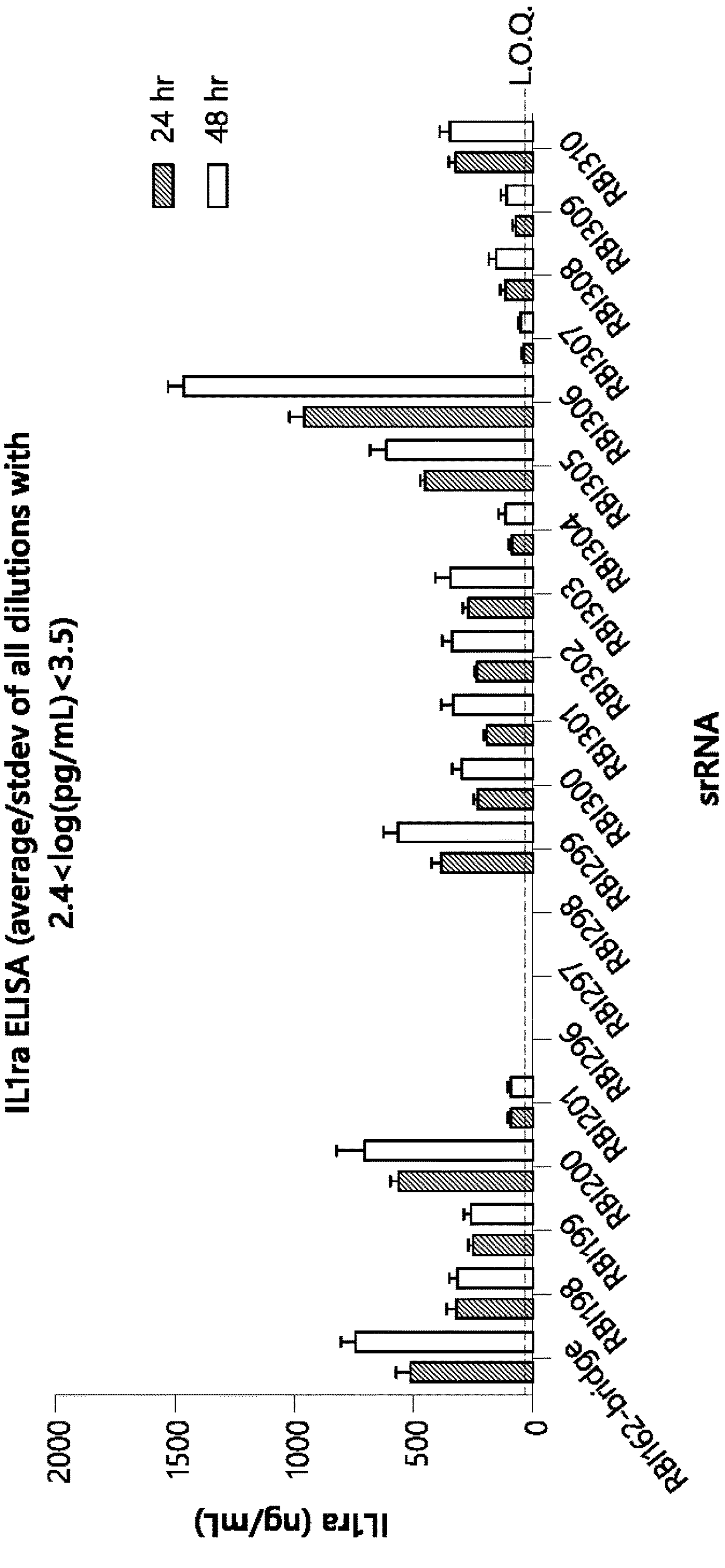
Figure 5A:
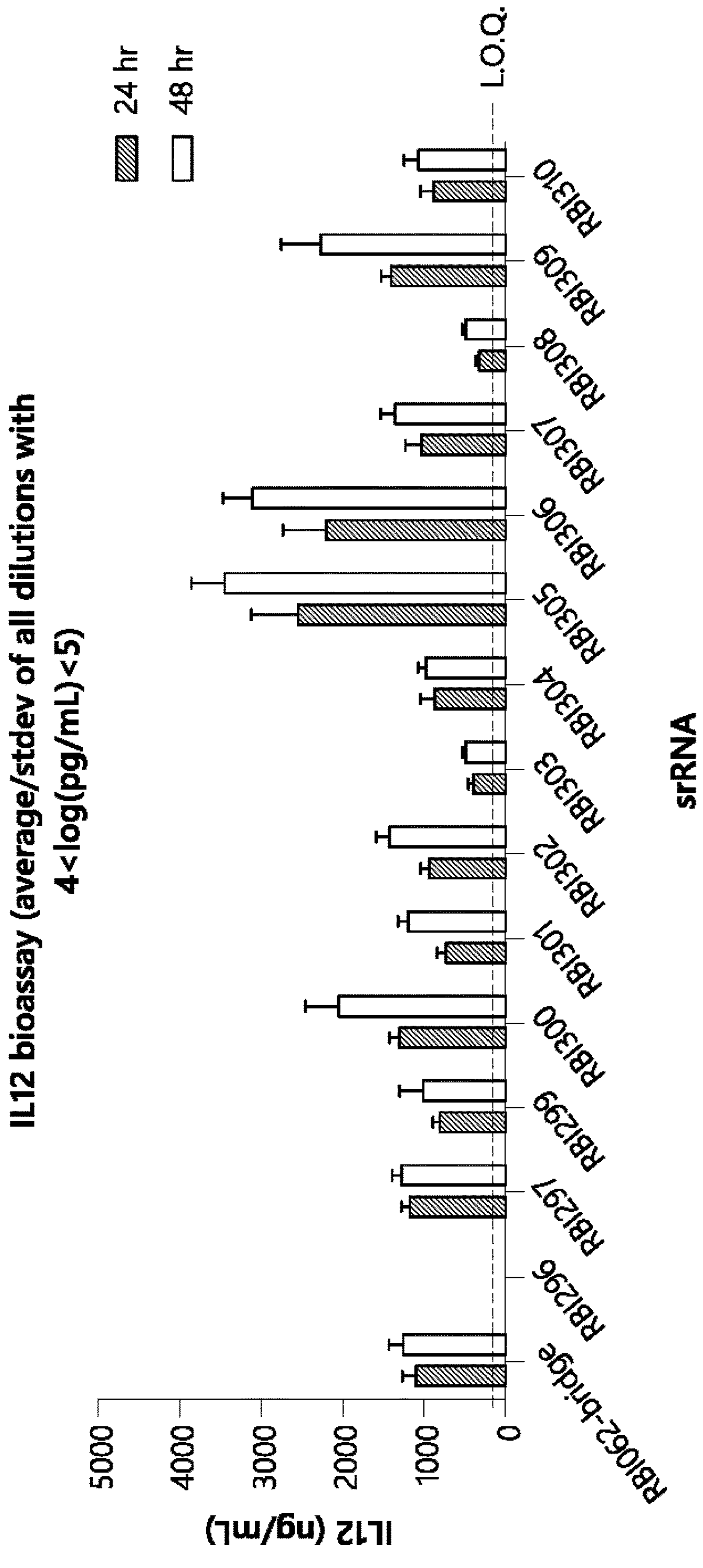
FIGS. 5A-5B are graphical representations of protein bioactivity from the two best multigenic configurations cloned into six different srRNA vectors.
Figure 5B:
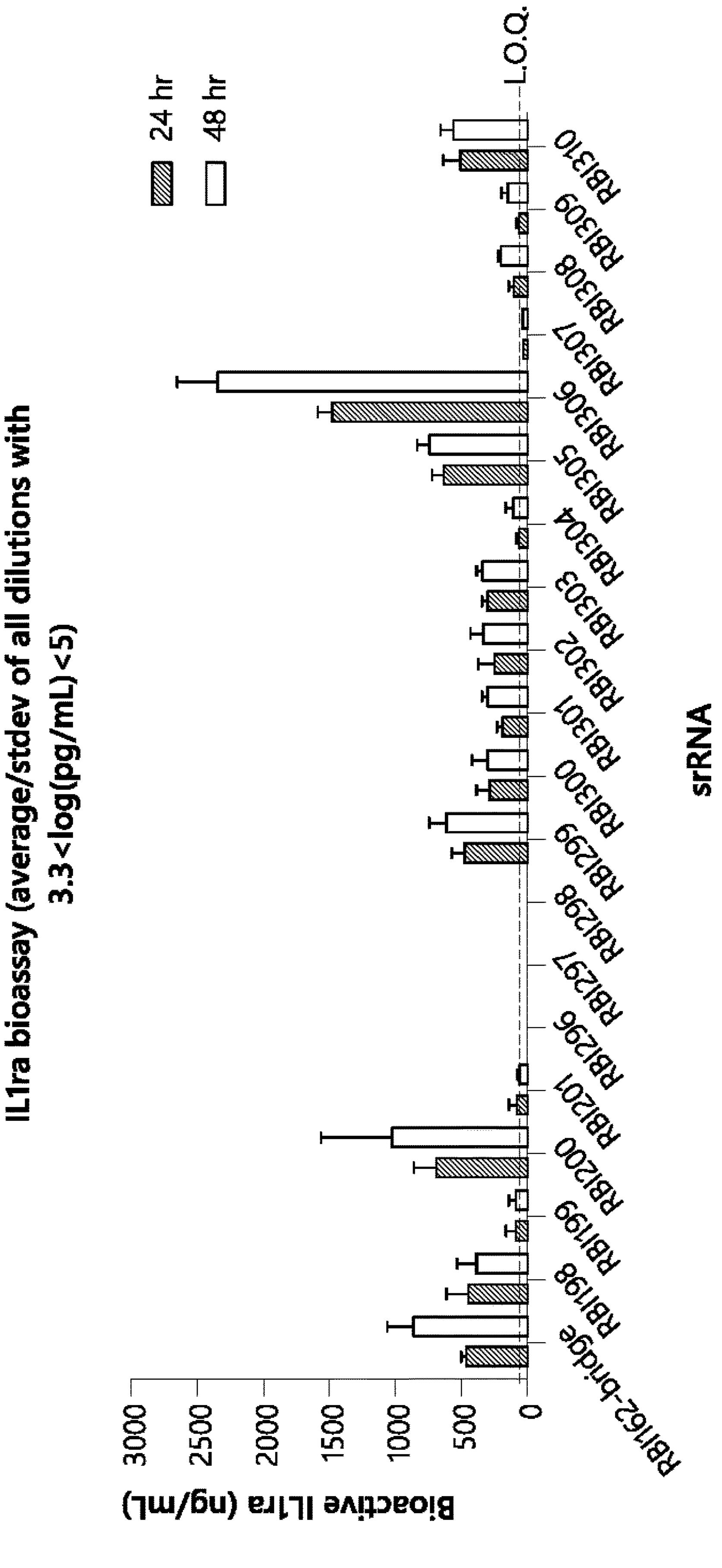

Results of mouse IL-12 and IL-1RA detecting ELISA assays as measured from transfected BHK-21 cells is shown in FIGS. 1A, 1B, 4A, and 4B. Different constructs, in either monogenic or multigenic form, having different ordinalities of IL-12 subunit p35, IL-12 subunit p40, and IL-1RA, were tested in order to determine which configuration of genes in the constructs yielded the most robust expression of IL-12 and IL-1RA. The Y-axis shows IL-12 or IL-1RA concentration in ng/mL. FIG. 3 shows the corresponding IL-12 and IL-1RA concentrations measured from each construct tested.

Figure 6:
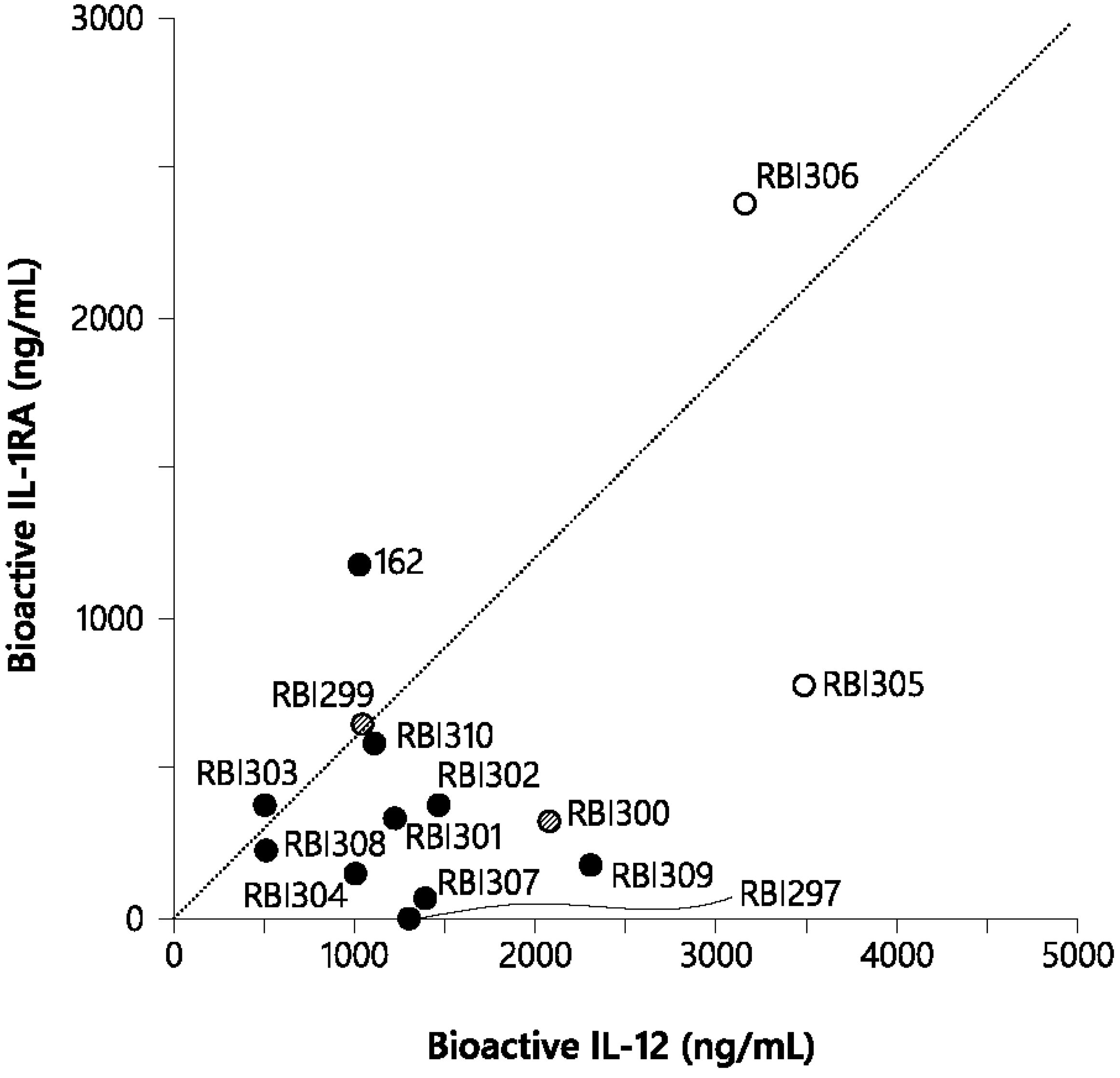
FIG. 6 is a graphical representation summarizing the IL-12 and IL-1RA bioactivity of the two best multigenic configurations in six different srRNA vectors.

Mouse IL-12 and IL-1RA detecting bioactivity was measured from supernatants of transfected BHK-21 cells with different srRNA constructs tested on reporter cells expressing different cytokine receptors. Results are shown in FIGS. 2A, 2B, 5A, and 5B. FIG. 6 shows the corresponding IL-12 and IL-1RA bioactivities measured from each construct tested.

Example 3

In Vivo Evaluation of Modified Alphavirus Vectors

This Example describes the results of in vivo experiments performed to evaluate the srRNA constructs described herein (e.g., both unformulated and LNP formulated vectors).

In these experiments, synthetic srRNA constructs derived from various alphavirus strains were designed and subsequently evaluated.

Mice and injections. BALB/c mice were purchased from Charles River Labs, Envigo, or Jackson Laboratories. On day of dosing, between 0.01-40 µg of material was injected intramuscularly either into one or split into both quadricep muscles. Vectors were administered either unformulated in saline, or LNP-formulated. Animals were monitored for body weight and other general observations throughout the course of the study. For pharmacokinetic studies, animals were dosed on Day 0 only.

LNP formulation. Replicon RNA was formulated in lipid nanoparticles using a microfluidics mixer and analyzed for particle size, polydispersity using dynamic light scattering and encapsulation efficiency. Lipids were suspended in ethanol. For L1, RNA was suspended in 10 mM citrate buffer pH 5.0 a concentration of 172 ug/ml, and was mixed at a flow rate of 3:1 (aqueous:organic). For L2, RNA was suspended in 250 mM NaOAc pH 4.0 at a concentration of 82 ug/ml, and was mixed at a flow rate of 3:1 (aqueous: organic).

ELISA. To measure the serum concentrations of IL-12 and IL-1RA, ELISA analysis was performed using Human IL-12 p70 DuoSet ELISA (RnD Systems cat #DY1270) and Human IL-1ra ELISA Kit (Abcam, ab211650) as per manufacturer's protocol.

Figure 7A:
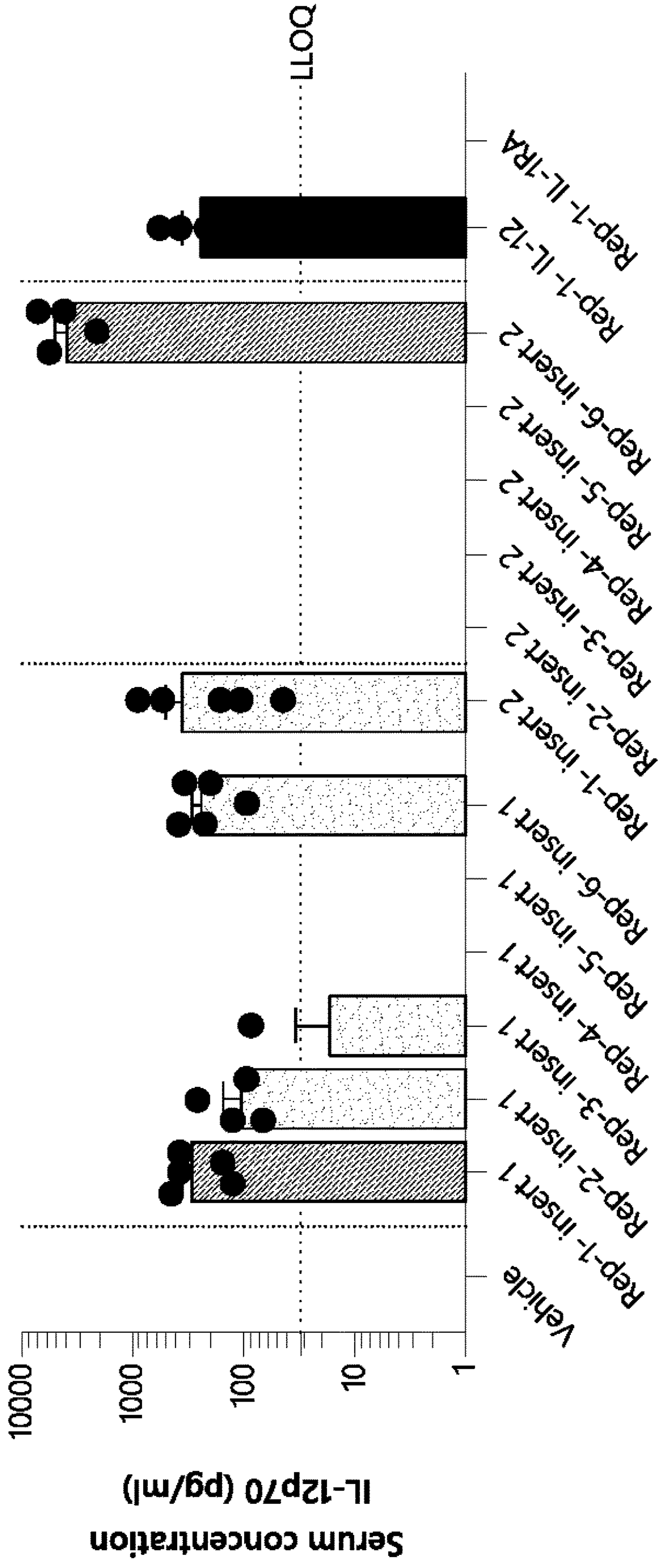
FIGS. 7A-7B are graphical representations of in vivo protein expression in mouse serum by the two best multigenic configurations in six different srRNA vectors.
Figure 7B:
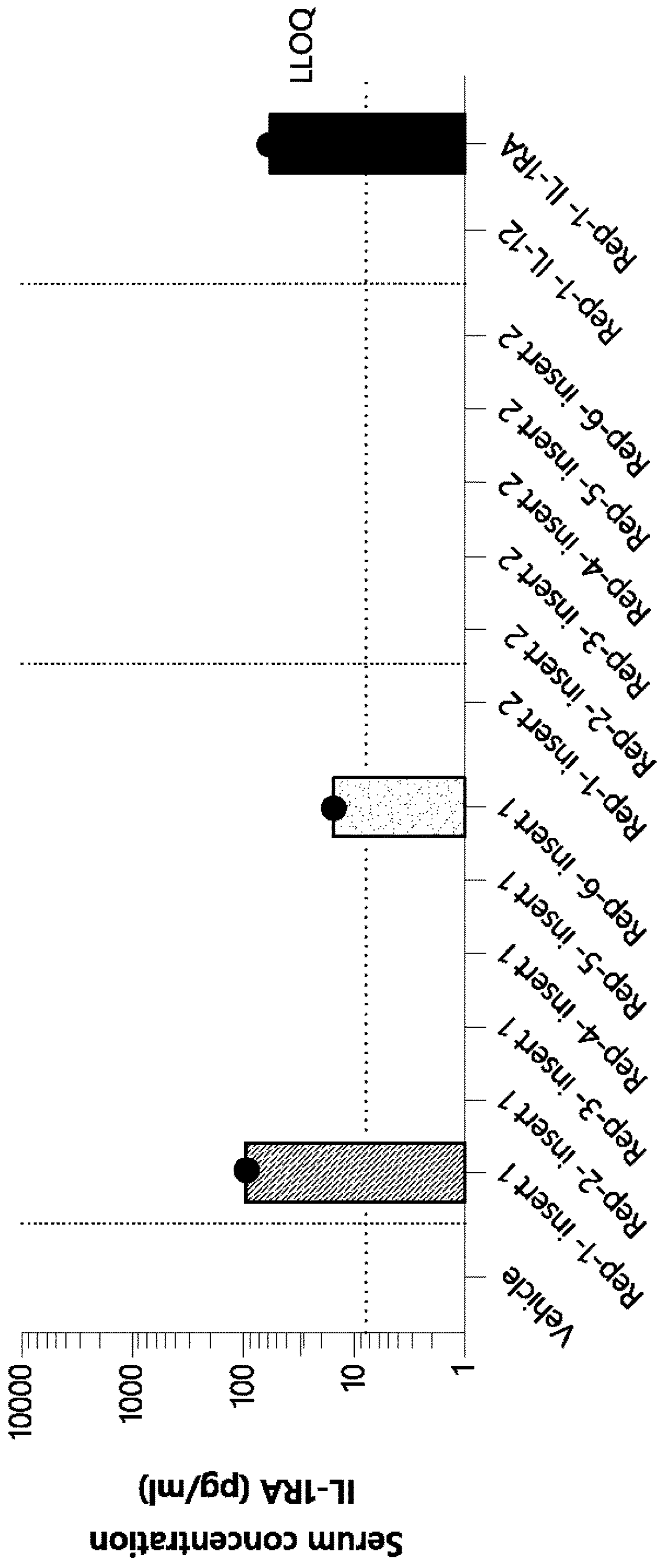

Evaluation of ordinality of genes and lipid formulation. The two best multigenic configurations from in vitro assays were then tested in six different srRNA vectors in vivo for protein expression in mouse serum. Results are shown in FIGS. 7A and 7B. Note that IL-1RA was not detected in some instances potentially due to short protein half-life.

Figure 8A:
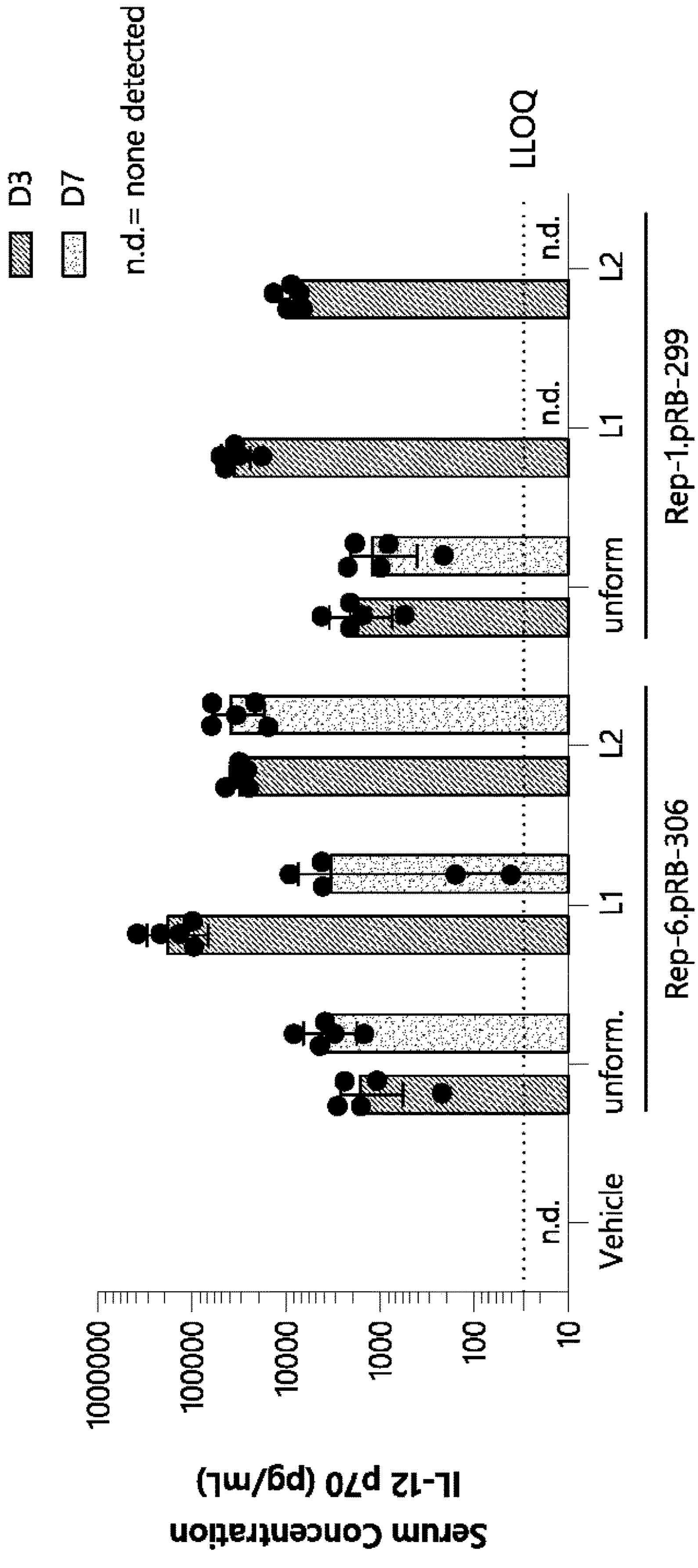
FIGS. 8A-8B are graphical representations of in vivo protein expression from different formulations of optimal srRNA constructs.
Figure 8B:
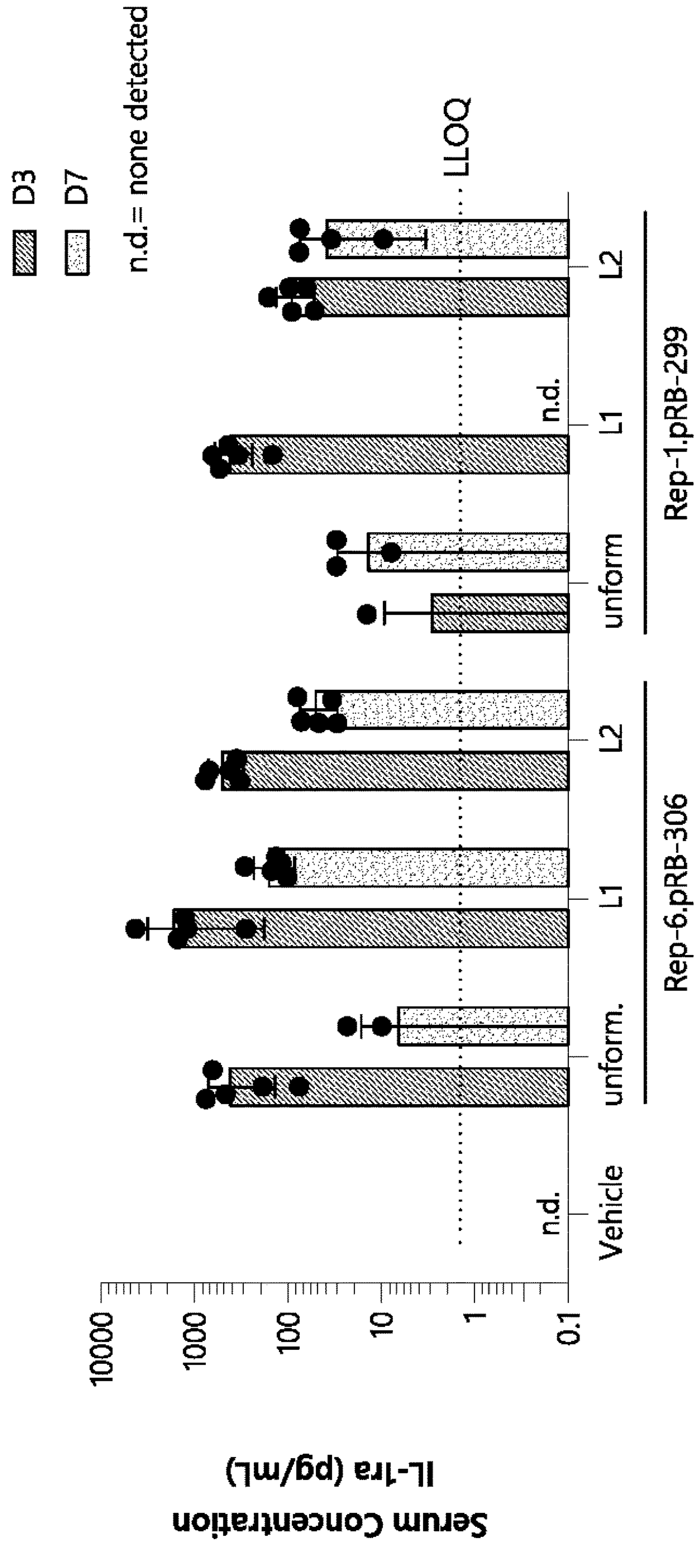

Multigenic configurations were then tested in different formulations and analyzed for protein expression in vivo by ELISA. Results are shown in FIGS. 8A and 8B.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A nucleic acid construct comprising a nucleic acid sequence encoding a modified alphavirus genome or self-replicating RNA (srRNA) obtained from an alphavirus genome or srRNA, wherein said modified alphavirus genome or srRNA is produced by replacing at least a portion of the nucleic acid sequence encoding the viral structural proteins of the alphavirus genome or srRNA with a coding sequence for a polypeptide construct comprising: a) a coding sequence for a p35 subunit of interleukin 12 (p35 or IL-12A) or a functional variant thereof; b) a coding sequence for a p40 subunit of interleukin 12 (p40 or IL-12B) or functional variant thereof; and c) a coding sequence for an interleukin-1 receptor antagonist (IL-1RA) or a functional variant thereof, wherein the coding sequences for IL-12A, IL-12B, and IL-1RA, or functional variants thereof, are operably linked to one another, and wherein the coding sequences for IL-12A, IL-12B, and IL-1RA express protein that is functional in a bioactivity assay, and wherein the nucleic acid sequence has at least 80%, at least 85%, at least 90%, at least 95%, at least 96%, at least 97%, at least 98%, at least 99%, or 100% sequence identity to the nucleic acid sequence of SEQ ID NO: 10.

2. The nucleic acid construct of claim 1, wherein the modified alphavirus genome or srRNA comprises no nucleic acid sequence encoding viral structural proteins.

3. The nucleic acid construct of claim 1, wherein the coding sequences of (a) through (c) are operably linked to one another within a single open reading frame or a polycistronic ORF.

4. The nucleic acid construct of claim 1, wherein the coding sequence encoding the polypeptide construct is operably linked to a promoter sequence.

5. The nucleic acid construct of claim 4, wherein the promoter sequence is a 26S subgenomic (sg) promoter.

6. The nucleic acid construct of claim 1, wherein the coding sequences of (a) through (c) are operably linked to one another by connector sequences comprising sequences encoding at least one of an autoproteolytic peptide and an internal ribosomal entry site (IRES).

7. The nucleic acid construct of claim 6, wherein the autoproteolytic peptide comprises one or more autoproteolytic cleavage sequences from a calcium-dependent serine endoprotease (furin), a porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

8. The nucleic acid construct of claim 6, wherein the IRES is a Kaposi's sarcoma-associated herpesvirus (KSHV) IRES, a hepatitis virus IRES, a Pestivirus IRES, a Cripavirus IRES, a *Rhopalosiphum padi* virus IRES, a fibroblast growth factor IRES, a platelet-derived growth factor IRES, a vascular endothelial growth factor IRES, an insulin-like growth factor IRES, a picornavirus IRES, an encephalomyocarditis virus (EMCV) IRES, a Pim-1 IRES, a p53 IRES, an Apaf-1 IRES, a TDP2 IRES, an L-myc IRES, or a c-myc IRES.

9. The nucleic acid construct of claim 1, wherein the alphavirus genome or srRNA is of an alphavirus belonging to the Venezuelan equine encephalitis virus/Eastern Equine Encephalitis virus (WEEV/EEEV) group, or the Semliki Forest virus (SFV) group, or the Sindbis virus (SINV) group.

10. The nucleic acid of claim 9, wherein the alphavirus is VEEV, EEEV, CHIKV, or SINV.

11. The nucleic acid construct of claim 1, wherein the polypeptide construct comprises, in N-terminus to C-terminus direction:

a) an IL-12A polypeptide, an IL-12B polypeptide, and an IL-1RA polypeptide; or;

b) an IL-1RA polypeptide, an IL-12B polypeptide, and an IL-12A polypeptide;

wherein the IL-12A, IL-12B, and IL-1RA polypeptides are operably linked to one another by one or more autoproteolytic cleavage sequences or IRES.

12. A recombinant cell comprising the nucleic acid construct according to claim 1.

13. The recombinant cell of claim 12, wherein the recombinant cell is a mammalian cell or an insect cell.

14. A pharmaceutical composition comprising a pharmaceutically acceptable excipient and the nucleic acid construct of claim 1.

15. The pharmaceutical composition of claim 14, wherein the composition is formulated with a delivery vehicle into a delivery system, wherein the delivery system comprises a liposome, a viral replicon particle (VRP), a lipid-based nanoparticle (LNP), a polymer nanoparticle, a physiologic buffer, a microsphere, an immune stimulating complex (ISCOM), a conjugate of bioactive ligand, or a combination of any thereof.

16. The pharmaceutical composition of claim 15, wherein the LNP delivery system comprises a cationic lipid, an ionizable cationic lipid, an anionic lipid, or a neutral lipid.

17. The pharmaceutical composition of claim 15, wherein the lipid is present in mass ratio of lipid to RNA from about 100:1 to about 4:1.

18. The pharmaceutical composition of claim 15, wherein the LNP have an average diameter of about 25 nm to about 1000 nm.

19. The pharmaceutical composition of claim 15, wherein the composition is formulated as a biotherapeutic.

* * * * *